US011311222B2

(12) United States Patent
Wybo

(10) Patent No.: US 11,311,222 B2
(45) Date of Patent: Apr. 26, 2022

(54) NEURAL LOCATING SYSTEM

(71) Applicant: Innovative Surgical Solutions, LLC, Wixom, MI (US)

(72) Inventor: Christopher Wybo, Brighton, MI (US)

(73) Assignee: Innovative Surgical Solutions, West Chester, PA (US)

(*) Notice: Subject to any disclaimer, the term of this patent is extended or adjusted under 35 U.S.C. 154(b) by 418 days.

(21) Appl. No.: 16/414,313

(22) Filed: May 16, 2019

(65) Prior Publication Data
US 2019/0269342 A1 Sep. 5, 2019

Related U.S. Application Data

(63) Continuation of application No. 15/286,333, filed on Oct. 5, 2016, now Pat. No. 10,321,833.

(51) Int. Cl.
*A61B 5/06* (2006.01)
*A61B 5/24* (2021.01)
(Continued)

(52) U.S. Cl.
CPC .............. *A61B 5/24* (2021.01); *A61B 5/0538* (2013.01); *A61B 5/061* (2013.01); *A61B 5/1104* (2013.01);
(Continued)

(58) Field of Classification Search
CPC ....... A61B 5/24; A61B 5/4029; A61B 5/1104; A61B 5/7425; A61B 5/294; A61B 5/1107;
(Continued)

(56) References Cited

U.S. PATENT DOCUMENTS

| 4,155,353 A | 5/1979 | Rea et al. |
| 4,493,327 A | 1/1985 | Bergelson et al. |

(Continued)

FOREIGN PATENT DOCUMENTS

| EP | 1417000 A2 | 5/2004 |
| EP | 2231003 A1 | 9/2010 |

(Continued)

OTHER PUBLICATIONS

International search report for international application No. EP17857966.
(Continued)

*Primary Examiner* — David J. McCrosky
(74) *Attorney, Agent, or Firm* — Quinn IP Law

(57) ABSTRACT

A nerve mapping system includes an elongate medical device, a non-invasive mechanical sensor, and a processor. The elongate medical device includes a distal end portion configured to explore an intracorporeal treatment area of a subject, and the distal end portion includes an electrode. The non-invasive mechanical sensor is configured to provide a mechanomyography output signal corresponding to a monitored mechanical response of a muscle innervated by the nerve. The processor is in communication with the electrode and the sensor, and is configured to provide a plurality of electrical stimuli to the electrode. Each of the plurality of stimuli is provided when the electrode is located at a different position within the intracorporeal treatment area. The processor determines the likelihood of a nerve existing at a particular point using the magnitudes of each of the stimuli and the detected response of the muscle.

17 Claims, 14 Drawing Sheets

(51) Int. Cl.
    *A61B 5/00*     (2006.01)
    *A61B 34/32*     (2016.01)
    *A61B 5/0538*     (2021.01)
    *B25J 9/16*     (2006.01)
    *A61B 34/30*     (2016.01)
    *A61B 5/11*     (2006.01)
    *A61B 5/294*     (2021.01)
    *A61B 34/10*     (2016.01)
    *A61B 18/00*     (2006.01)

(52) U.S. Cl.
    CPC ............ *A61B 5/1107* (2013.01); *A61B 5/294* (2021.01); *A61B 5/4029* (2013.01); *A61B 5/4519* (2013.01); *A61B 5/4893* (2013.01); *A61B 5/6852* (2013.01); *A61B 5/7425* (2013.01); *A61B 34/30* (2016.02); *A61B 34/32* (2016.02); *B25J 9/1666* (2013.01); *A61B 5/6885* (2013.01); *A61B 2018/00071* (2013.01); *A61B 2018/00964* (2013.01); *A61B 2034/105* (2016.02); *A61B 2034/107* (2016.02)

(58) Field of Classification Search
    CPC ....... A61B 5/061; A61B 34/30; A61B 5/4893; A61B 5/4519; A61B 2018/00071; A61B 2018/00964; A61B 2034/105; A61B 2034/107; B25J 9/1666
    See application file for complete search history.

(56) References Cited

U.S. PATENT DOCUMENTS

| | | |
|---|---|---|
| 4,807,642 A | 2/1989 | Brown |
| 4,940,453 A | 7/1990 | Cadwell |
| 4,994,015 A | 2/1991 | Cadwell |
| 5,047,005 A | 9/1991 | Cadwell |
| 5,078,674 A | 1/1992 | Cadwell |
| 5,116,304 A | 5/1992 | Cadwell |
| 5,178,145 A | 1/1993 | Rea |
| 5,482,038 A | 1/1996 | Ruff |
| 5,566,678 A | 10/1996 | Cadwell |
| 5,593,429 A | 1/1997 | Ruff |
| 5,631,667 A | 5/1997 | Cadwell |
| 5,775,331 A | 7/1998 | Raymond et al. |
| 5,860,939 A | 1/1999 | Wofford et al. |
| 5,888,370 A | 3/1999 | Becker et al. |
| 5,993,630 A | 11/1999 | Becker et al. |
| 5,993,632 A | 11/1999 | Becker et al. |
| 6,030,401 A | 2/2000 | Marino |
| 6,093,205 A | 7/2000 | McLeod et al. |
| 6,181,961 B1 | 1/2001 | Prass |
| 6,183,518 B1 | 2/2001 | Ross et al. |
| 6,206,921 B1 | 3/2001 | Guagliano et al. |
| 6,221,082 B1 | 4/2001 | Marino et al. |
| 6,224,603 B1 | 5/2001 | Marino |
| 6,251,140 B1 | 6/2001 | Marino et al. |
| 6,264,659 B1 | 7/2001 | Ross et al. |
| 6,266,394 B1 | 7/2001 | Marino |
| 6,266,558 B1 | 7/2001 | Gozani et al. |
| 6,280,447 B1 | 8/2001 | Marino et al. |
| 6,287,832 B1 | 9/2001 | Becker et al. |
| 6,290,724 B1 | 9/2001 | Marino |
| 6,312,443 B1 | 11/2001 | Stone |
| 6,368,325 B1 | 4/2002 | McKinley et al. |
| 6,387,070 B1 | 5/2002 | Marino et al. |
| 6,387,130 B1 | 5/2002 | Stone et al. |
| 6,436,143 B1 | 8/2002 | Ross et al. |
| 6,466,817 B1 | 10/2002 | Kaula et al. |
| 6,478,805 B1 | 11/2002 | Marino et al. |
| 6,485,518 B1 | 11/2002 | Cornwall et al. |
| 6,491,626 B1 | 12/2002 | Stone et al. |
| 6,500,128 B2 | 12/2002 | Marino |
| 6,519,319 B1 | 2/2003 | Marino et al. |
| 6,530,930 B1 | 3/2003 | Marino et al. |
| 6,533,797 B1 | 3/2003 | Stone et al. |
| 6,540,747 B1 | 4/2003 | Marino |
| 6,564,078 B1 | 5/2003 | Marino et al. |
| 6,638,281 B2 | 10/2003 | Gorek |
| 6,641,708 B1 | 11/2003 | Becker et al. |
| 6,654,634 B1 | 11/2003 | Prass |
| 6,739,112 B1 | 5/2004 | Marino |
| 6,760,616 B2 | 7/2004 | Hoey et al. |
| 6,764,452 B1 | 7/2004 | Gillespie et al. |
| 6,764,489 B2 | 7/2004 | Ferree |
| 6,802,844 B2 | 10/2004 | Ferree |
| 6,805,668 B1 | 10/2004 | Cadwell |
| 6,843,790 B2 | 1/2005 | Ferree |
| 6,852,126 B2 | 2/2005 | Ahlgren |
| 6,870,109 B1 | 3/2005 | Villarreal |
| 6,887,248 B2 | 5/2005 | McKinley et al. |
| 6,923,814 B1 | 8/2005 | Hildebrand et al. |
| 6,945,973 B2 | 9/2005 | Bray |
| 6,964,674 B1 | 11/2005 | Matsuura et al. |
| 6,981,990 B2 | 1/2006 | Keller |
| 7,001,432 B2 | 2/2006 | Keller et al. |
| 7,025,769 B1 | 4/2006 | Ferree |
| 7,050,848 B2 | 5/2006 | Hoey et al. |
| 7,072,521 B1 | 7/2006 | Cadwell |
| 7,079,883 B2 | 7/2006 | Marino et al. |
| 7,160,303 B2 | 1/2007 | Keller |
| 7,162,850 B2 | 1/2007 | Marino et al. |
| 7,166,113 B2 | 1/2007 | Arambula et al. |
| 7,175,662 B2 | 2/2007 | Link et al. |
| 7,177,677 B2 | 2/2007 | Kaula et al. |
| 7,207,949 B2 | 4/2007 | Miles et al. |
| 7,214,197 B2 | 5/2007 | Prass |
| 7,214,225 B2 | 5/2007 | Ellis et al. |
| 7,230,688 B1 | 6/2007 | Villarreal |
| 7,267,691 B2 | 9/2007 | Keller et al. |
| 7,296,500 B1 | 11/2007 | Martinelli |
| 7,320,689 B2 | 1/2008 | Keller |
| 7,338,531 B2 | 3/2008 | Ellis et al. |
| 7,341,590 B2 | 3/2008 | Ferree |
| 7,367,958 B2 | 5/2008 | McBean et al. |
| 7,374,448 B1 | 5/2008 | Jepsen et al. |
| 7,379,767 B2 | 5/2008 | Rea |
| 7,470,236 B1 | 12/2008 | Kelleher et al. |
| 7,485,146 B1 | 2/2009 | Crook et al. |
| 7,522,953 B2 | 4/2009 | Kaula et al. |
| 7,527,629 B2 | 5/2009 | Link et al. |
| 7,527,649 B1 | 5/2009 | Blain |
| 7,553,307 B2 | 6/2009 | Bleich et al. |
| 7,555,343 B2 | 6/2009 | Bleich |
| 7,569,067 B2 | 8/2009 | Keller |
| 7,578,819 B2 | 8/2009 | Bleich et al. |
| 7,582,058 B1 | 9/2009 | Miles et al. |
| 7,583,991 B2 | 9/2009 | Rea |
| 7,611,522 B2 | 11/2009 | Gorek |
| 7,618,423 B1 | 11/2009 | Valentine et al. |
| 7,628,813 B2 | 12/2009 | Link |
| 7,634,315 B2 | 12/2009 | Cholette |
| 7,657,308 B2 | 2/2010 | Miles et al. |
| 7,664,544 B2 | 2/2010 | Miles et al. |
| 7,666,195 B2 | 2/2010 | Kelleher et al. |
| 7,691,057 B2 | 4/2010 | Miles et al. |
| 7,693,562 B2 | 4/2010 | Marino et al. |
| 7,708,776 B1 | 5/2010 | Blain et al. |
| 7,713,463 B1 | 5/2010 | Reah et al. |
| 7,722,613 B2 | 5/2010 | Sutterlin et al. |
| 7,722,673 B2 | 5/2010 | Keller |
| 7,738,968 B2 | 6/2010 | Bleich |
| 7,738,969 B2 | 6/2010 | Bleich |
| 7,740,631 B2 | 6/2010 | Bleich et al. |
| 7,766,816 B2 | 8/2010 | Chin et al. |
| 7,776,049 B1 | 8/2010 | Curran et al. |
| 7,776,094 B2 | 8/2010 | McKinley et al. |
| 7,785,248 B2 | 8/2010 | Annest et al. |
| 7,785,253 B1 | 8/2010 | Arambula et al. |
| 7,815,682 B1 | 10/2010 | Peterson et al. |
| 7,819,801 B2 | 10/2010 | Miles et al. |
| 7,828,855 B2 | 11/2010 | Ellis et al. |
| 7,833,251 B1 | 11/2010 | Ahlgren et al. |
| 7,857,813 B2 | 12/2010 | Schmitz et al. |

(56) References Cited

U.S. PATENT DOCUMENTS

| | | |
|---|---|---|
| 7,862,592 B2 | 1/2011 | Peterson et al. |
| 7,862,614 B2 | 1/2011 | Keller et al. |
| 7,867,277 B1 | 1/2011 | Tohmeh |
| 7,883,527 B2 | 2/2011 | Matsuura et al. |
| 7,887,538 B2 | 2/2011 | Bleich et al. |
| 7,887,568 B2 | 2/2011 | Ahlgren |
| 7,887,595 B1 | 2/2011 | Pimenta |
| 7,892,173 B2 | 2/2011 | Miles et al. |
| 7,901,430 B2 | 3/2011 | Matsuura et al. |
| 7,905,840 B2 | 3/2011 | Pimenta et al. |
| 7,905,886 B1 | 3/2011 | Curran et al. |
| 7,914,350 B1 | 3/2011 | Bozich et al. |
| 7,918,849 B2 | 4/2011 | Bleich et al. |
| 7,918,891 B1 | 4/2011 | Curran et al. |
| 7,920,922 B2 | 4/2011 | Gharib et al. |
| 7,927,337 B2 | 4/2011 | Keller |
| 7,935,051 B2 | 5/2011 | Miles et al. |
| 7,938,830 B2 | 5/2011 | Saadat et al. |
| 7,942,104 B2 | 5/2011 | Butcher et al. |
| 7,942,826 B1 | 5/2011 | Scholl et al. |
| 7,946,236 B2 | 5/2011 | Butcher |
| 7,959,577 B2 | 6/2011 | Schmitz et al. |
| 7,962,191 B2 | 6/2011 | Marino et al. |
| 7,963,915 B2 | 6/2011 | Bleich |
| 7,963,927 B2 | 6/2011 | Kelleher et al. |
| 7,981,144 B2 | 7/2011 | Geist et al. |
| 7,991,463 B2 | 8/2011 | Kelleher et al. |
| 8,000,782 B2 | 8/2011 | Gharib et al. |
| 8,005,535 B2 | 8/2011 | Gharib et al. |
| 8,012,212 B2 | 9/2011 | Link et al. |
| 8,016,767 B2 | 9/2011 | Miles et al. |
| 8,027,716 B2 | 9/2011 | Gharib et al. |
| 8,048,080 B2 | 11/2011 | Bleich et al. |
| 8,050,769 B2 | 11/2011 | Gharib et al. |
| 8,055,349 B2 | 11/2011 | Gharib et al. |
| 8,062,298 B2 | 11/2011 | Schmitz et al. |
| 8,062,300 B2 | 11/2011 | Schmitz et al. |
| 8,062,369 B2 | 11/2011 | Link |
| 8,062,370 B2 | 11/2011 | Keller et al. |
| 8,063,770 B2 | 11/2011 | Costantino |
| 8,068,912 B2 | 11/2011 | Kaula et al. |
| 8,070,812 B2 | 12/2011 | Keller |
| 8,074,591 B2 | 12/2011 | Butcher et al. |
| 8,075,601 B2 | 12/2011 | Young |
| 8,083,685 B2 | 12/2011 | Fagin et al. |
| 8,083,796 B1 | 12/2011 | Raiszadeh et al. |
| 8,088,163 B1 | 1/2012 | Kleiner |
| 8,088,164 B2 | 1/2012 | Keller |
| 8,090,436 B2 | 1/2012 | Hoey et al. |
| 8,092,455 B2 | 1/2012 | Neubardt et al. |
| 8,092,456 B2 | 1/2012 | Bleich et al. |
| 8,103,339 B2 | 1/2012 | Rea |
| 8,114,019 B2 | 2/2012 | Miles et al. |
| 8,114,162 B1 | 2/2012 | Bradley |
| 8,123,668 B2 | 2/2012 | Annest et al. |
| 8,133,173 B2 | 3/2012 | Miles et al. |
| 8,137,284 B2 | 3/2012 | Miles et al. |
| 8,147,421 B2 | 4/2012 | Farquhar et al. |
| 8,147,551 B2 | 4/2012 | Link et al. |
| 8,165,653 B2 | 4/2012 | Marino et al. |
| 8,167,915 B2 | 5/2012 | Ferree et al. |
| 8,172,750 B2 | 5/2012 | Miles et al. |
| 8,206,312 B2 | 6/2012 | Farquhar |
| 8,255,044 B2 | 8/2012 | Miles et al. |
| 8,255,045 B2 | 8/2012 | Gharib et al. |
| 8,303,515 B2 | 11/2012 | Miles et al. |
| 8,337,410 B2 | 12/2012 | Kelleher et al. |
| 8,343,079 B2 | 1/2013 | Bartol et al. |
| 8,394,129 B2 | 3/2013 | Morgenstern Lopez et al. |
| 8,500,653 B2 | 8/2013 | Farquhar |
| 8,500,738 B2 | 8/2013 | Wolf, II |
| 8,535,224 B2 | 9/2013 | Cusimano Reaston et al. |
| 8,538,539 B2 | 9/2013 | Gharib et al. |
| 8,556,808 B2 | 10/2013 | Miles et al. |
| 8,562,539 B2 | 10/2013 | Marino |
| 8,562,660 B2 | 10/2013 | Peyman |
| 8,568,317 B1 | 10/2013 | Gharib et al. |
| 8,591,431 B2 | 11/2013 | Calancie et al. |
| 8,641,638 B2 | 2/2014 | Kelleher et al. |
| 8,731,654 B2 | 5/2014 | Johnson et al. |
| 8,784,330 B1 | 7/2014 | Scholl et al. |
| 8,792,977 B2 | 7/2014 | Kakei et al. |
| 8,855,822 B2 | 10/2014 | Bartol et al. |
| 8,864,654 B2 | 10/2014 | Kleiner et al. |
| 8,936,626 B1 | 1/2015 | Tohmeh et al. |
| 8,945,004 B2 | 2/2015 | Miles et al. |
| 8,958,869 B2 | 2/2015 | Kelleher et al. |
| 8,983,593 B2 | 3/2015 | Bartol et al. |
| 8,989,855 B2 | 3/2015 | Murphy et al. |
| 8,989,866 B2 | 3/2015 | Gharib et al. |
| 9,014,776 B2 | 4/2015 | Marino et al. |
| 9,014,797 B2 | 4/2015 | Shiftman et al. |
| 9,037,250 B2 | 5/2015 | Kaula et al. |
| 9,066,701 B1 | 6/2015 | Finley et al. |
| 9,084,551 B2 | 7/2015 | Brunnett et al. |
| 9,131,947 B2 | 9/2015 | Ferree |
| 9,192,415 B1 | 11/2015 | Arnold et al. |
| 9,295,396 B2 | 3/2016 | Gharib et al. |
| 9,295,401 B2 | 3/2016 | Cadwell |
| 9,301,711 B2 | 4/2016 | Bartol et al. |
| 9,392,953 B1 | 7/2016 | Gharib |
| 9,446,259 B2 | 9/2016 | Phillips et al. |
| 2007/0232958 A1 | 10/2007 | Donofrio et al. |
| 2011/0270121 A1 | 11/2011 | Johnson et al. |
| 2013/0123659 A1 | 5/2013 | Bartol et al. |
| 2013/0197321 A1 | 8/2013 | Wilson |
| 2013/0204097 A1 | 8/2013 | Rondoni et al. |
| 2014/0020178 A1 | 1/2014 | Stashuk et al. |
| 2014/0088029 A1 | 3/2014 | Sugimoto et al. |
| 2014/0121555 A1 | 5/2014 | Scott et al. |
| 2014/0148725 A1 | 5/2014 | Cadwell |
| 2014/0163411 A1 | 6/2014 | Rea |
| 2014/0275926 A1 | 9/2014 | Scott et al. |
| 2014/0276195 A1 | 9/2014 | Papay et al. |
| 2014/0358026 A1 | 12/2014 | Mashiach et al. |
| 2015/0045783 A1 | 2/2015 | Edidin |
| 2015/0051506 A1 | 2/2015 | Wybo et al. |
| 2015/0088029 A1* | 3/2015 | Wybo ............... A61B 5/1104 600/554 |
| 2015/0112325 A1 | 4/2015 | Whitman |
| 2015/0230749 A1 | 8/2015 | Gharib et al. |
| 2015/0342521 A1 | 12/2015 | Narita et al. |
| 2015/0342621 A1 | 12/2015 | Jackson, III |
| 2016/0051812 A1 | 2/2016 | Montgomery, Jr. et al. |
| 2016/0143556 A1 | 5/2016 | Farquhar et al. |
| 2016/0206363 A1 | 7/2016 | Mehta et al. |

FOREIGN PATENT DOCUMENTS

| | | |
|---|---|---|
| EP | 2535082 A1 | 12/2012 |
| WO | WO2014160832 A2 | 10/2014 |
| WO | WO2015171619 A1 | 11/2015 |
| WO | WO2016100340 A1 | 6/2016 |

OTHER PUBLICATIONS

J. Herdmann MD; V. Deletis MD PhD; H.Edmonds PhD; N. Morota MD, Spinal Cord and Nerve Root Monitoring in Spine Surgery and Related Procedures, Spine Journal, Apr. 1, 1996, pp. 879-885, vol. 21.

N. Hollands MB, BS; J. Kostuik. Continuous Electromyographic Moniotring to Detect Nerve Root Injury During Thoracolumbar Scoliosis Surgery, Spine Journal, Nov. 1, 1997, pp. 2547-2550, vol. 22, Issue 21.

C. Harper, J. Daube, Facial Nerve Electromyography and Other Cranial Nerve Monitoring, Journal of Clinical Neurophysiology, May 1998, pp. 206-216, vol. 15, Issue 3.

D. Beck, J. Ben Ecke Jr, Intraoperative Facial Nerve Monitoring Technical Aspects, Official Journal of the American Academy of Otolaryngology-Head and Neck Surgery Foundation, Apr. 27, 1989.

W. Welch MD, R. Rose PhD, J. Balzer Phd, G. Jacobs, MD, Evaluation with evoked and spontaneous electromyography during

(56) References Cited

OTHER PUBLICATIONS lumbar instrumentation: a prospective study, Journal of Neurosurgery, Sep. 1997, pp. 397-402, vol. 87, No. 3.
W. Young MD, D. Morledge PhD, W. Martin PhD, K. Park MD, Intraoperative Stimulation of Pedicle Screws a New Method for Verification of Screw Placement, Journal of Neurosurgery, 1995, pp. 544 547 vol. 44.
K. Sugita MD, S. Kobayashi MD, Technical and instrumental improvements in the surgical treatment of acoustic neurinomas, Journal of Neurosurgery, Dec. 1982, pp. 747-752, vol. 57.
J. Boston, L. Deneault, Sensory evoked potentials: a system for clinical testing and patient monitoring, International Journal of Clinical Monitoring and Computing, 1984, pp. 13-19, Martinus Nijhoff Publishers, Netherlands.
A. Moller, Neuromonitoring in Operations in the Skull Base, The Keio Journal of Medicine, Oct. 1991, pp. 151-159.
J. Maurer, H. Pelster, W. Mann, Intraoperatives Monitoring motorischer Hurnnerven bei Operationen an Hals und Schadelbasis, Laryngo-Rhino-Otol, pp. 561-567, vol. 73.
N. Friedman MD, M. Curran R. Ept, Somatosensory Evoked Potentials after Sequential Extremity Stimulation: A New Method for Improved Monitoring Accuracy, Neurosurgery, 1987, pp. 755-758, vol. 21, No. 5.
R. Gopalan, P. Parker, R. Scott, Microprocessor-Based System for Monitoring Spinal Evoked Potentials During Surgery, IEEE Transactions on Biomedical Engineering, Oct. 1986, pp. 982-985, vol. BME-22, No. 10.
B. Moed MD, B. Ahmad MD, J. Craig MD, G. Jacobson PhD, M. Anders MD, Intraoperative Monitoring with Stimulus-Evoked Electromyography during Placement Iliosacral Screws, The Journal of Bone and Joint Surgery, Apr. 1998, pp. 537-546, vol. 80-A, No. 4, The Journal of Bone and Joint Surgery, Inc.
C. Yingling PhD, J. Gardi PhD, Intraoperative Monitoring of Facial and Cochlear Nerves During Acoustic Neuroma Surgery, Acoustic Neuroma I, Apr. 1992, pp. 413-448, vol. 25, No. 2, Otolaryngologic Clinics of North America.
N. Holland MB, BS, J. Kostuik MD, Continuous Electromyographic Monitoring to Detect Nerve Root Injury During Thoracolumbar Scoliosis Surgery, Spine, 1997, pp. 2547-2550, vol. 22, No. 21, Lippincott-Raven Publishers.
P. Dulguerov, F. Marchal, W. Lehmann, Postparotidectomy Facial Nerve Paralysis: Possible Etiologic Factors and Results with Routine Facial Nerve Monitoring, The Laryngoscope, May 1999, pp. 754-762 vol. 109, Lippincott Williams & Wilkins, Inc. Philadelphia, Pennsylvania.
M. Imai MS, Y. Harada MD, Y. Atsuta MD, Y. Takemitsu MD, T. Iwahara MD, Automated Spinal Cord Monitoring for Spinal Surgery, Paraplegia, 1989, pp. 204-211.
R. Witt, Facial nerve monitoring in parotid surgery: The standard of care?, Otolaryngology-Head and Neck Surgery, Nov. 1998, pp. 468-470, vol. 119, No. 5.
CPEL1950897P Chinese Examination Report dated Jun. 10, 2021 for Application No. 201780061967.2, filed Oct. 13, 2017 by Applicant Innovative Surgical Solutions, LLC.

\* cited by examiner

NEURAL LOCATING SYSTEM

CROSS REFERENCE TO RELATED APPLICATIONS

The present application is a continuation of U.S. patent application Ser. No. 15/286,333, which was published as US 2018/0092559, and which is incorporated by reference in its entirety.

TECHNICAL FIELD

The present disclosure relates generally to a surgical diagnostic system for detecting the presence of one or more nerves.

BACKGROUND

Traditional surgical practices emphasize the importance of recognizing or verifying the location of nerves to avoid injuring them. Advances in surgical techniques include development of techniques with ever smaller exposures, such as minimally invasive surgical procedures, and the insertion of ever more complex medical devices. With these advances in surgical techniques, there is a corresponding need for improvements in methods of detecting and/or avoiding nerves during surgery.

SUMMARY

In one embodiment, a method of locating a nerve within an intracorporeal treatment area of a subject begins by providing a first, "searching" electrical stimulus at a first location within the intracorporeal treatment area. The first electrical stimulus has a first current magnitude that does not induce a threshold response of a muscle innervated by the nerve. As a stimulating probe is advanced, a second, searching electrical stimulus is provided at a second location within the intracorporeal treatment area. The second electrical stimulus has the same current magnitude as the first stimulus and induces a response of the muscle that is greater than the threshold.

Following application of the second, inducing stimulus, one or more additional "locating" electrical stimuli are provided at the second location, each with a current magnitude less than the first stimulus. From these one or more additional electrical stimuli, a minimum current magnitude is determined that is required to induce the threshold response of the muscle at the second location. This minimum current magnitude is then used to determine a distance from the second location to the nerve.

In another embodiment, a first, searching electrical stimulus may be applied at a first location within the intracorporeal treatment area. The first location is greater than a threshold distance from the nerve, wherein the threshold distance is the greatest distance at which the first electrical stimulus can induce a threshold response of a muscle that is innervated by the nerve.

A second, locating electrical stimulus may then be applied at a second location within the intracorporeal treatment area. The second, locating stimulus has a current magnitude less than the current magnitude of the first, searching stimulus, and the second location is closer to the nerve than the first location. The magnitude of a response of a muscle to the locating electrical stimulus may be monitored and, together with the magnitude of the locating stimulus, may be used to determine a distance from the second location to the nerve.

Each of the first location and the second location may be registered within a virtual workspace, where a portion of the virtual workspace surrounding the first location is indicated as not containing the nerve, and the presence of a nerve within the virtual workspace may be indicated at the determined distance from the second location.

The above features and advantages and other features and advantages of the present disclosure are readily apparent from the following detailed description of the best modes for carrying out the disclosure when taken in connection with the accompanying drawings.

"A," "an," "the," "at least one," and "one or more" are used interchangeably to indicate that at least one of the item is present; a plurality of such items may be present unless the context clearly indicates otherwise. All numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; about or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range. Each value within a range and the endpoints of a range are hereby all disclosed as separate embodiment.

DETAILED DESCRIPTION

Figure 1:
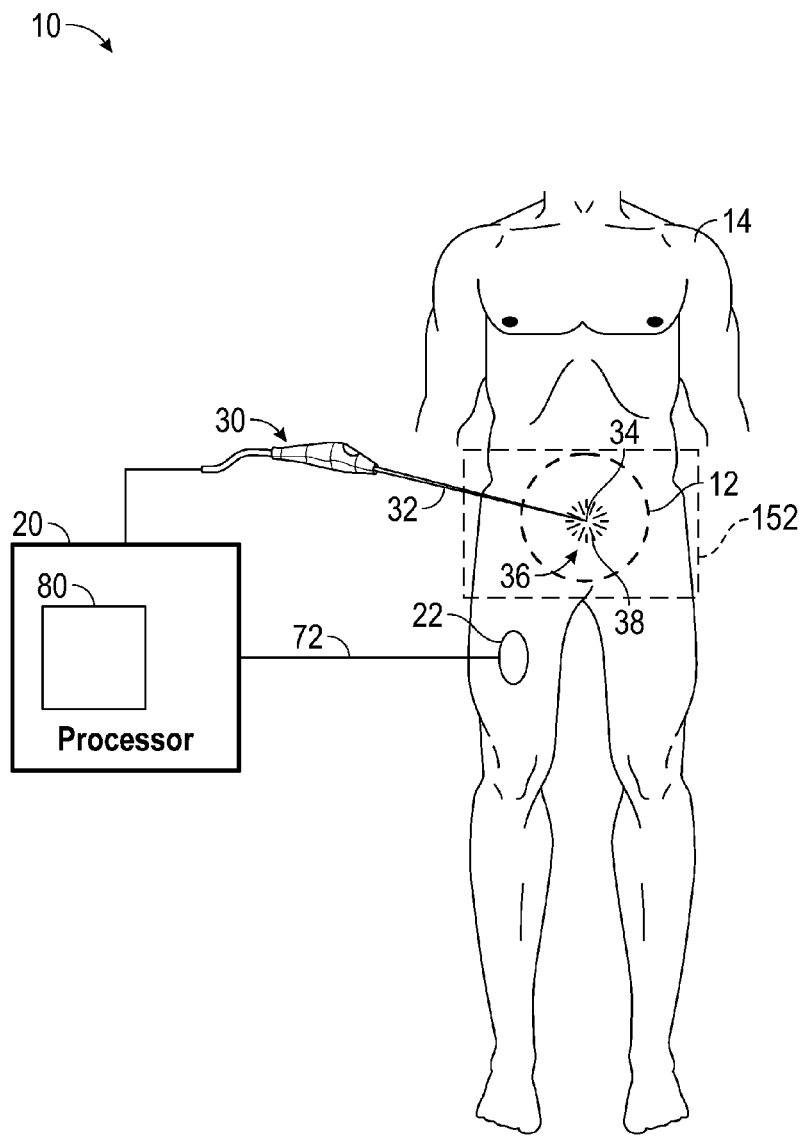
FIG. 1 is a schematic diagram of a neural monitoring system for detecting an artificially-induced mechanical muscle response.

Referring to the drawings, wherein like reference numerals are used to identify like or identical components in the various views, FIG. 1 schematically illustrates a neural monitoring system 10 that may be used to identify the presence of one or more nerves within an intracorporeal treatment area 12 of a subject 14. As will be described in greater detail below, in one configuration, the system 10 may monitor one or more muscles of the subject 14 for a mechanical motion, and may be capable of determining whether the mechanical motion is an artificially-induced mechanical response of a muscle to a provided stimulus (also referred to as an "artificially-induced mechanical muscle response") or a motion cause by another factor (e.g., a subject-intended muscle contraction/relaxation and/or an environmentally caused movement). If an artificially-induced mechanical muscle response is detected during the procedure, the system 10 may provide an indication to a user, such as via a display or perform another appropriate action.

As used herein, an artificially-induced mechanical muscle response refers to a contraction or relaxation of a muscle in response to a stimulus that is not received through natural sensory means (e.g., sight, sound, taste, smell, and touch). Instead, it is a contraction/relaxation of a muscle that is induced by the application of a stimulus directly to a nerve that innervates the muscle. Examples of stimuli that may cause an "artificially-induced" muscle response may include an electrical current applied directly to the nerve or to intracorporeal tissue or fluid immediately surrounding the nerve. In this example, if the applied electrical current is sufficiently strong and/or sufficiently close to the nerve, it may artificially cause the nerve to depolarize (resulting in a corresponding contraction of the muscle innervated by that nerve). Other examples of such "artificial stimuli" may involve mechanically-induced depolarization (e.g., physically stretching or compressing a nerve, such as with a tissue retractor), thermally-induced depolarization (e.g., through ultrasonic cautery), or chemically-induced depolarization (e.g., through the application of a chemical agent to the tissue surrounding the nerve).

During an artificially-induced mechanical muscle response, a muscle innervated by the artificially depolarized nerve may physically contract or relax (i.e., a mechanical response). Such a mechanical reaction may primarily occur along a longitudinal direction of the muscle (i.e., a direction aligned with the constituent fibers of the muscle), though may further result in a respective swelling/relaxing of the muscle in a lateral direction (which may be substantially normal to the skin for most skeletal muscles). This local movement of the muscle during an artificially-induced mechanical muscle response may be measured relative to the position of the muscle when in a non-stimulated state, and is distinguished from other global translations of the muscle.

The neural monitoring system 10 may include a processor 20 that is in communication with at least one mechanical sensor 22. The mechanical sensor 22 may include, for example, a strain gauge, a force transducer, a position encoder, an accelerometer, a piezoelectric material, or any other transducer or combination of transducers that may convert a physical motion into a variable electrical signal.

Each mechanical sensor 22 may specially be configured to monitor a local mechanical movement of a muscle of the subject 14. For example, each sensor 22 may include a fastening means, such as an adhesive material/patch, that allows the sensor 22 to be adhered, bandaged, or otherwise affixed to the skin of the subject 14 (i.e. affixed on an external skin surface). Other examples of suitable fastening means may include bandages, sleeves, or other elastic fastening devices that may hold the sensor 22 in physical contact with the subject 14. Alternatively, the mechanical sensor 22 (and/or coupled device) may be configured to monitor a local mechanical movement of a muscle by virtue of its physical design. For example, the sensors/coupled devices may include catheters, balloons, bite guards, orifice plugs or endotracheal tubes that may be positioned within a lumen or natural opening of the subject to monitor a response of the lumen or orifice, or of a muscle that is directly adjacent to and/or connected with the lumen or orifice. In a preferred embodiment, the mechanical sensor is a non-invasive device, whereby the term "non-invasive" is intended to mean that the sensor is not surgically placed within the body of the subject (i.e., via cutting of tissue to effectuate the placement). For the purposes of this disclosure, non-invasive sensors may include sensors that are placed within naturally occurring body lumens that are accessible without the need for an incision.

In one configuration, the sensor 22 may include a contact detection device, that may provide an indication if the sensor 22 is in physical contact with the skin of the subject 14. The contact detection device may, for example, include a pair of electrodes that are configured to contact the skin of the subject 14 when the sensor 22 is properly positioned. The sensor 22 and/or contact detection device may then monitor an impedance between the electrodes to determine whether the electrodes are in contact with the skin. Other examples of suitable contact detection devices may include capacitive touch sensors or buttons that protrude slightly beyond the surface of the sensor.

The system 10 may further include one or more elongate medical instruments 30 that are capable of selectively providing a stimulus within the intracorporeal treatment area 12 of the subject 14 (i.e., also referred to as a stimulator 30). For example, in one configuration, the elongate medical instrument 30 may include a probe 32 (e.g., a ball-tip probe, k-wire, or needle) that has one or more electrodes 34 disposed on a distal end portion 36. The electrode(s) 34 may be selectively electrified, at either the request of a user/physician, or at the command of the processor 20, to provide an electrical stimulus 38 to intracorporeal tissue of the subject 14. For some procedures, the elongate medical instrument 30 may include a dialator, retractor, clip, cautery probe, pedicle screw, or any other medical instrument that may be used in an invasive medical procedure. Regardless of the instrument, if the intended artificial stimulus is an electrical current, the instrument 30 may include one or more selectively electrifiable electrodes 34 disposed at a portion of the instrument that is intended to contact tissue within the intracorporeal treatment area 12 during a procedure.

During a surgical procedure, the user/surgeon may selectively administer the stimulus to intracorporeal tissue within the treatment area 12 to identify the presence of one or more nerve bundles or fibers. For an electrical stimulus 38, the user/surgeon may administer the stimulus, for example, upon depressing a button or foot pedal that is in communication with the system 10, and more specifically in communication with the stimulator 30. The electrical stimulus 38 may, for example, be a discrete pulse (e.g., a step pulse) having a pulse width within the range of about 30 µs to about 500 µs. In other examples, the discrete pulse may have a pulse width within the range of about 50 µs to about 200 µs, or within the range of about 75 µs to about 125 µs. The discrete pulse may be periodically applied at a frequency of, for example, between about 1 Hz and about 10 Hz.

Figure 2:
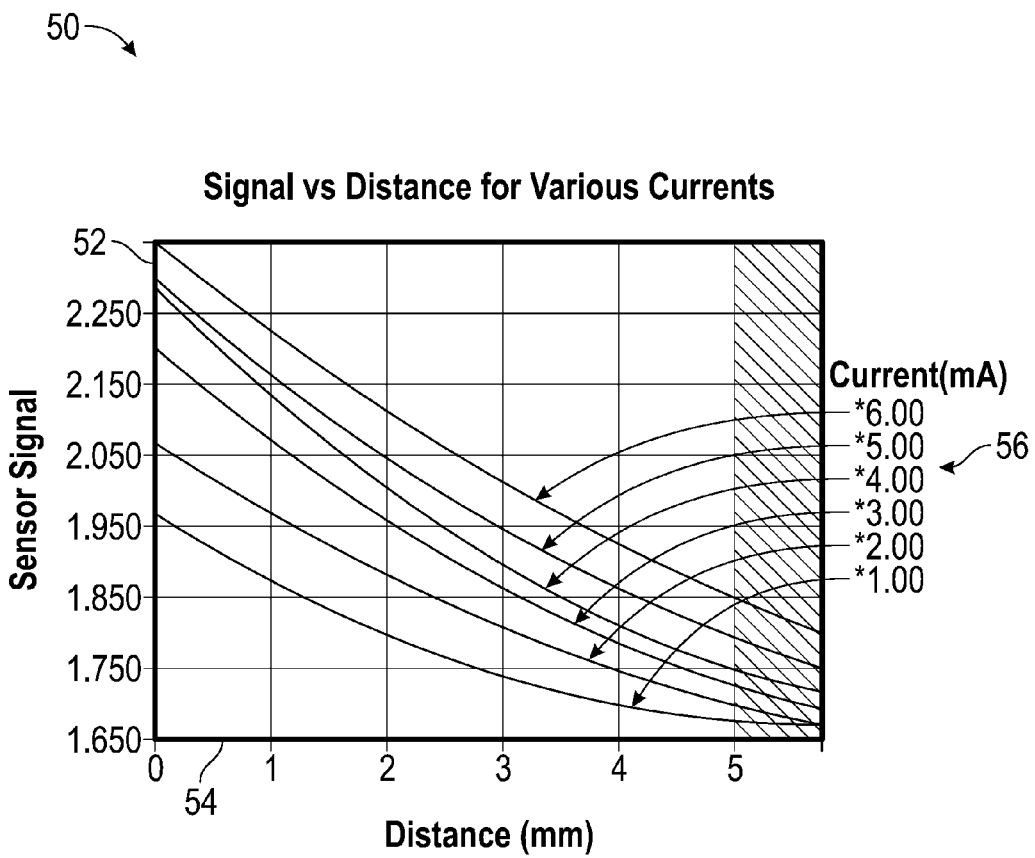
FIG. 2 is a schematic graph of the relationship between MMG output signal amplitude, stimulator electrical current, and distance between a stimulator electrode and a nerve.

If a nerve extends within a predetermined distance of the electrode 34, the electrical stimulus 38 may cause the nerve to depolarize, resulting in a mechanical twitch of a muscle that is innervated by the nerve (i.e., an artificially-induced mechanical muscle response). In general, the magnitude of the response/twitch may be directly correlated to the distance between the electrode and the nerve, and the magnitude of the stimulus current. FIG. 2 illustrates a graph 50 of these relationships where the magnitude 52 of the sensed response is shown as a function of the distance 54 between the stimulator and the nerve, and the magnitude 56 of the applied electrical current stimulus. In one configuration, the relationships illustrated in FIG. 2 (or variants thereof) may be stored in a lookup table associated with the processor 20. The lookup table may then be employed by the processor 20 to provide an approximate distance 54 between the electrode 34 and the nerve, given a known stimulus magnitude 56 and a measured mechanical muscle response magnitude 52.

Referring again to FIG. 1, prior to beginning a surgical procedure, the one or more mechanical sensors 22 may be placed in mechanical communication with one or more muscles of the subject 14. In the present context, a sensor 22 may be in mechanical communication with the muscle if it can physically detect a movement, velocity, acceleration, strain or other physical response of the muscle, either via direct contact with the muscle, or via a mechanical relationship through one or more intermediate materials and/or tissues (e.g., skin and/or subcutaneous tissue).

Figure 3:
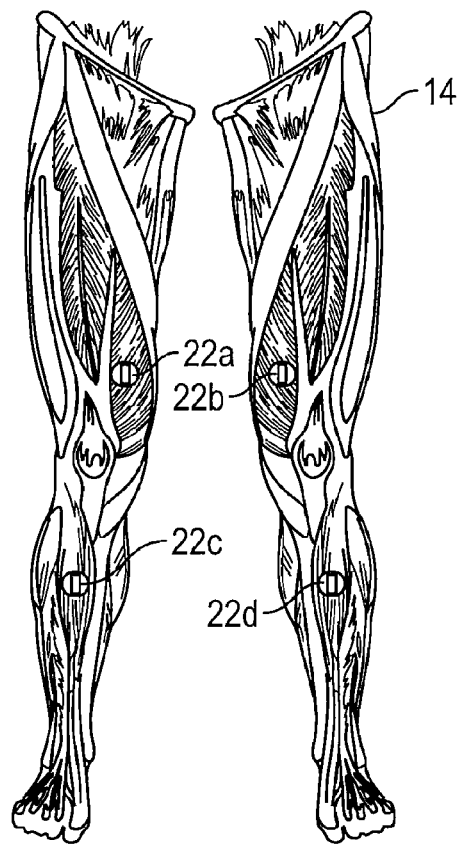
FIG. 3 is a schematic front view of the placement of a plurality of mechanical sensors on the legs of a subject.
Figure 4:
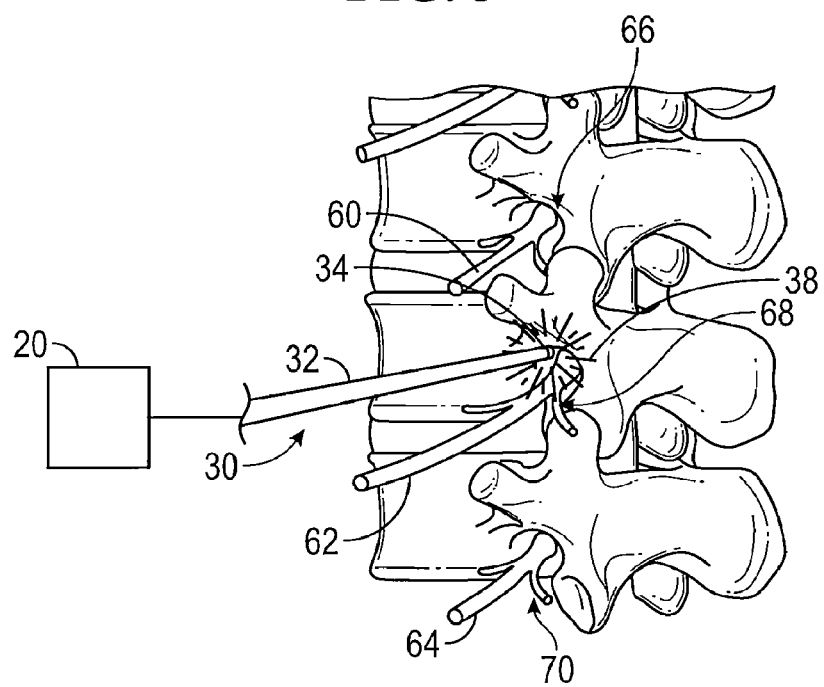
FIG. 4 is a schematic side view of an intracorporeal treatment area including a portion of the lumbar spine.

FIG. 3 illustrates an example of the placement of a plurality of mechanical sensors 22 for a surgical procedure that may occur proximate the L2, L3, and/or L4 vertebrae of the lumbar spine (shown schematically in FIG. 4). The nerves 60, 62 and 64 exiting the L2, L3 and L4 foramen 66, 68, 70 may therefore either lie within the treatment area 12 (i.e., the area surrounding the L2, L3, and/or L4 vertebrae), or may be immediately proximate to this area. Using common anatomical knowledge, the surgeon may understand that damage to these nerves 60, 62, 64 may affect the functioning of the vastus medialis muscles and the tibialis anterior muscles. As such, the surgeon may place mechanical sensors 22a-22d on or near the vastus medialis muscles and the tibialis anterior muscles to guard against inadvertent manipulation of the nerves during the procedure. For example, mechanical sensors 22a and 22b are placed on the vastus medialis muscles, which are innervated by the nerves 60, 62 exiting the L2 and L3 foramen 66, 68, and sensors 22c and 22d are placed on the tibialis anterior muscles, which are innervated by the nerves 64 exiting the L4 foramen 70.

In general, each mechanical sensor 22 may generate a mechanomyography (MMG) output signal (schematically shown in FIG. 1 at 72) that corresponds to a sensed mechanical movement/response of the adjacent muscle. The MMG output signal 72 may be either a digital or analog signal, and may typically be provided to the processor 20 through either wired or wireless communication means (e.g., through a physical wire, or using radio frequency communication protocols, such as according to IEEE 802.11 or another protocol such as BLUETOOTH (a communication standard set forth by the Bluetooth Special Interest Group)). As a specific signal, the MMG output signal 72 is intended to be separate and distinct from any electrical potentials of the muscle or skin (often referred to as electromyography (EMG) signals). While electrical (EMG) and mechanical (MMG) muscle responses may be related, their relationship is complex, and not easily described (e.g., electrical potentials are very location specific, with a potentially variable electrical potential across the volume of the muscle of interest).

Referring again to FIG. 1, the processor 20 may be in communication with the stimulator 30 and the mechanical sensor 22, and may be configured to receive the MMG output signal 72 from the mechanical sensor 22. The processor 20 may be embodied as one or multiple digital computers, data processing devices, and/or digital signal processors (DSPs), which may have one or more microcontrollers or central processing units (CPUs), read only memory (ROM), random access memory (RAM), electrically-erasable programmable read only memory (EEPROM), a high-speed clock, analog-to-digital (A/D) circuitry, digital-to-analog (D/A) circuitry, input/output (I/O) circuitry, and/or signal conditioning and buffering electronics.

The processor 20 may be configured to automatically perform one or more signal processing algorithms 80 or methods to determine whether a sensed mechanical movement (i.e., via the MMG output signal 72) is representative of an artificially-induced mechanical muscle response or if it is merely a subject-intended muscle movement and/or an environmentally caused movement. These processing algorithms 80 may be embodied as software or firmware, and may either be stored locally on the processor 20, or may be readily assessable by the processor 20.

During an invasive procedure, as discussed above, the processor 20 may determine the distance between an electrically stimulating electrode 34 and a nerve by providing an electrical stimulus 38 to the electrode 34 at a known or measurable current magnitude, and by measuring the magnitude of the mechanical muscle response. In one configuration, a surgeon may be able to surmise the relative location of the nerve by dithering the stimulator 30, and monitoring the changes in the magnitude of the response (i.e., moving the stimulator 30 closer to the nerve would yield a greater response). In another embodiment, the system 10 may be configured to automatically determine the position of the nerve relative to the stimulator 30 without the need for mechanical dithering. For example, the stimulator 30 may be provided with a plurality of electrodes that may collectively be used to triangulate the position of the nerve.

It is preferable that any electrodes disposed on the stimulator 30 are configured to make leading contact with intracorporeal tissue as the probe is being advanced in a longitudinal direction. This maximizes the likelihood that each electrode will remain in contact with the tissue. Examples of designs that place the electrodes on a leading surface include, for example, positioning an electrode on a tip of the probe, positioning an electrode on a sloped or conical advancing face, and/or extending/protruding the electrode radially outward from a perimeter surface.

Figure 5:
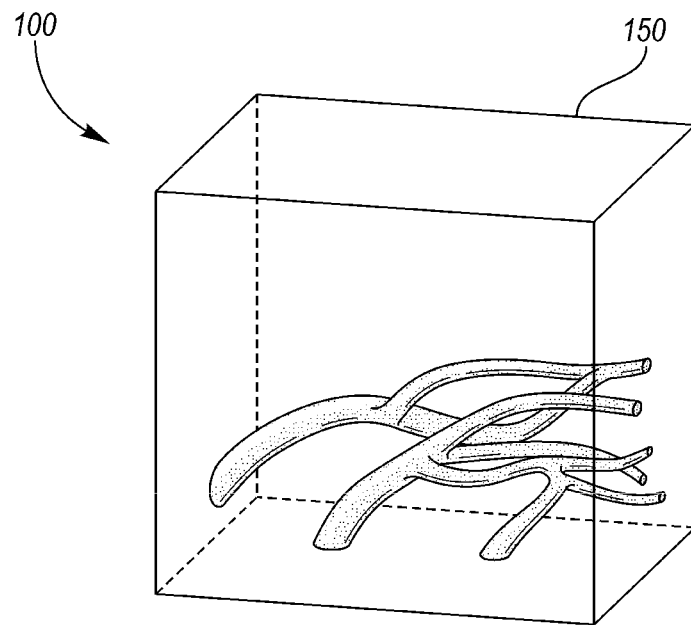
FIG. 5 is a schematic isometric view of a virtual nerve probability model.

While the above-described technology is useful in providing a real-time directional reference to a user, in a further extension, the processor 20 may be configured to create and maintain a three-dimensional nerve model 100, such as shown in FIG. 5.

Figure 6:
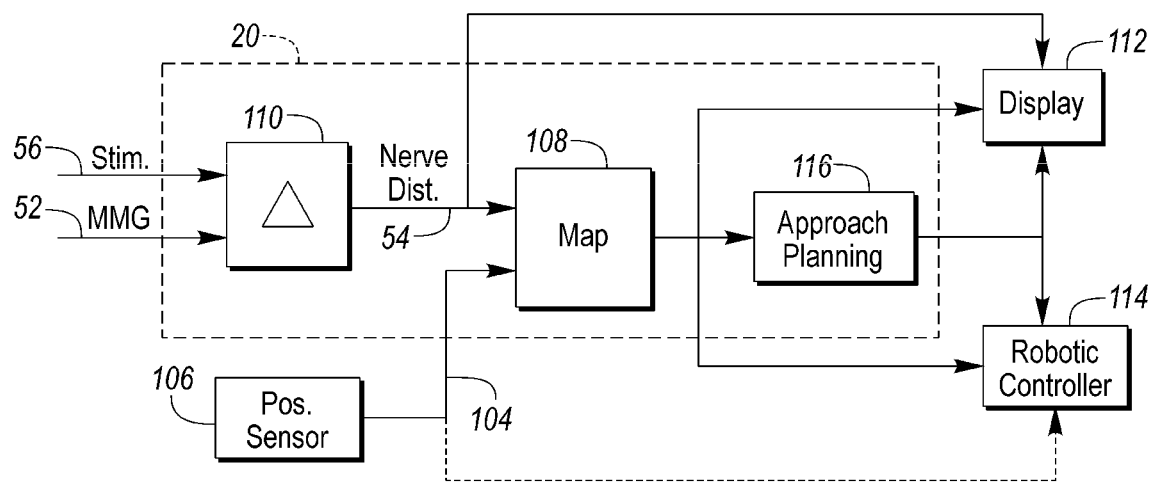
FIG. 6 is a schematic data flow diagram for creating and utilizing a 3D nerve model.

FIG. 6 schematically illustrates a data flow diagram for creating and utilizing a 3D nerve model. As shown, the processor 20 may utilize a determined distance 54 between a stimulator electrode 34 and a nerve, together with a known position 104 of the electrode 34 as determined by a position sensor, locating device, or kinematic algorithm (generally at 106), to build a 3D nerve probability model at 108. As discussed above, the determined distance 54 may be a function of the stimulus intensity 56 and the amplitude of the MMG response 52, and may be determined at 110 using established relationships, such as shown in FIG. 2. In one configuration the processor 20 may use these relationships to directly solve for distance 54 given a variable stim current 56 and a variable MMG response 52. In another configuration, the processor 20 may establish a threshold MMG response level that is indicative of a "response" and then may determine the minimum stim current 56 that is required to induce this threshold response. From this minimum current, distance may be easily computed and/or inferred.

Once created, the nerve model 100 may be output via a display at 112, provided to a robotic controller at 114, or passed to an approach planning module 116 (which, in turn, may output to the display 112 and/or robotic controller 114). The displayed model may be, for example, either viewed as a stand-alone model, or merged with other imagery. If passed to the robotic controller 114 directly, the model 100 may, for example, inform feed-forward robotic control techniques to provide more accurate and dynamic tool control in the proximity of nerves. The approach planning module 116 may be software-implemented and may merge the nerve model 100 with a separate anatomical model to optimize an ideal tool path/surgical approach toward an anatomical target. Finally, in some configurations, determined nerve distance 54 may also be displayed to a user at 112 as an informational metric.

In one configuration, the processor 20 may build the three-dimensional nerve model 100 (at 108) by sampling/stimulating at differing locations within the intraoperative space to triangulate nerve position and progressively construct and/or refine the nerve model 100. In one configuration, this triangulation may be performed using geometric equations (i.e., where a triangle can be constructed between the nerve and two known stimulation locations, and the location of the nerve can be resolved by knowing the distances between all three vertices of the triangle). In another embodiment, a model-based triangulation approach may be performed, such as schematically illustrated in FIGS. 7, 9A-9D, and 10A-10B. This model-based triangulation approach may prove less computationally intensive for model building than the geometric equation-based alternative.

Figure 7:
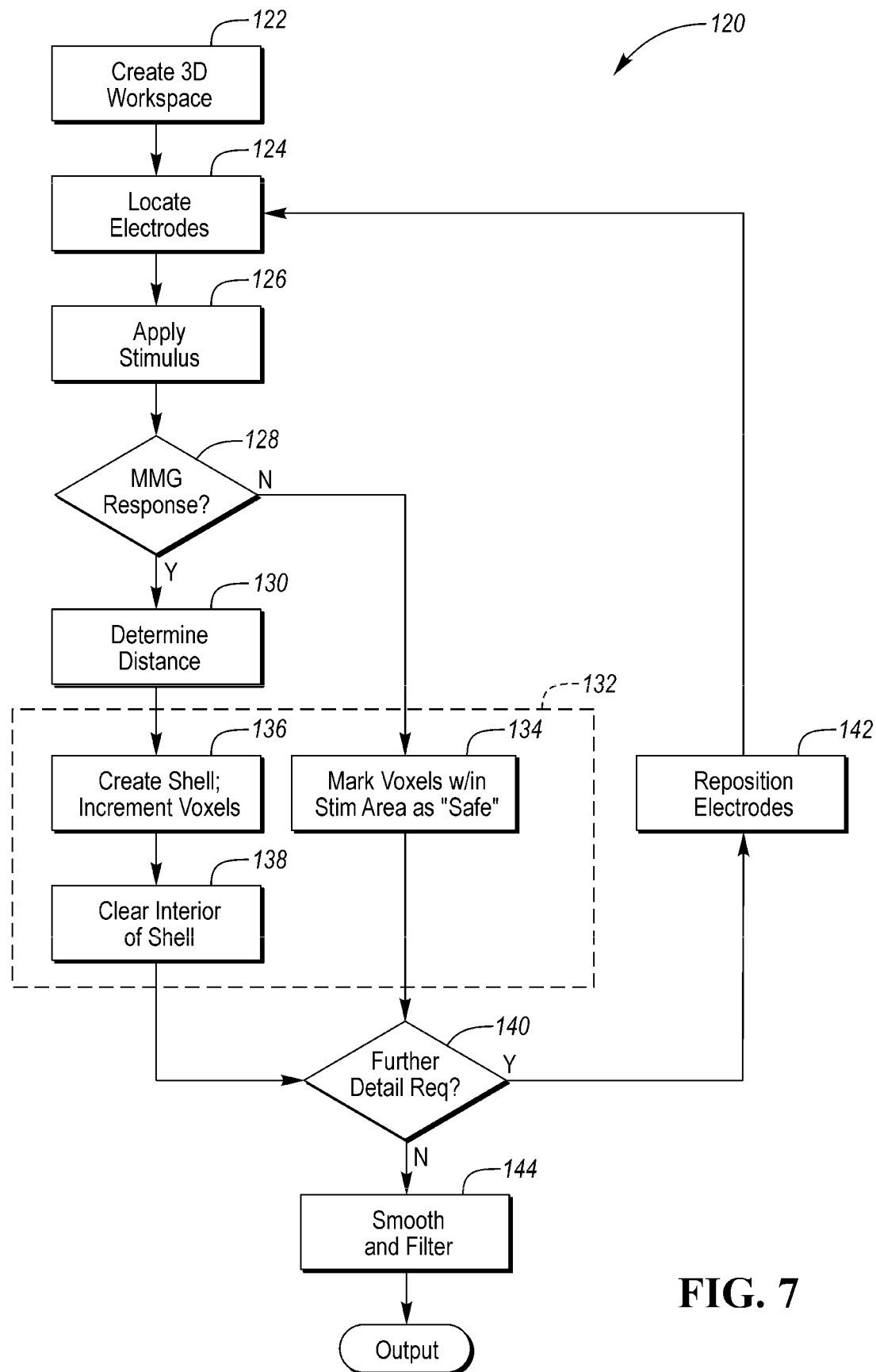
FIG. 7 is a schematic flow chart illustrating a method of constructing a nerve probability model.

The method 120 schematically illustrated in FIG. 7 generally operates on the assumption that a stimulator electrode 34 transmits current to the surrounding tissue in a generally uniform, omnidirectional manner. As such, if a nerve is stimulated, and a distance determined (in the manner described above), the nerve may exist at some location on a shell that surrounds the electrode at the determined distance. Conversely, if no threshold muscle response is detected, it can be assumed that no nerve exists within a radius of the electrode that is defined by the stimulus magnitude. By aggregating shells constructed from a plurality of electrode locations, the system may define areas that are more likely to represent nerves based on the density of recorded shells. In effect, this is a model-based triangulation method.

The method 120 may begin by segmenting a virtual 3D workspace 150 (shown in FIG. 5) into a plurality of voxels (at 122). As is well understood in computer graphics and modeling, a "voxel" is a three-dimensional, volumetric element that is a defined subdivision of a larger volume (i.e., much in the same way that a 2D pixel is a defined subdivision of a larger 2D area or image). Each voxel may have a spatial location relative to the surrounding voxels, and may be capable of holding an assigned value. The virtual 3D workspace 150 may be registered with a corresponding physical 3D workspace 152 (illustrated in FIG. 1) that includes the intraoperative site 12. Registration generally involves establishing a relationship between the coordinate spaces of the two workspaces such that there is direct correspondence. In the case of a robotic surgical procedure, the virtual workspace 150 may be coincident with, for example, the physical workspace 152 that is accessible by the robot.

Once the virtual workspace 150 is created and registered to the physical workspace 152, one or more stimulation electrodes 34 within the physical workspace may then be registered/located within the virtual workspace 150 (at 124). In one configuration, electrode position within the physical 3D workspace 152 may be determined by a locating device 106 and/or kinematic algorithm.

Figure 8:
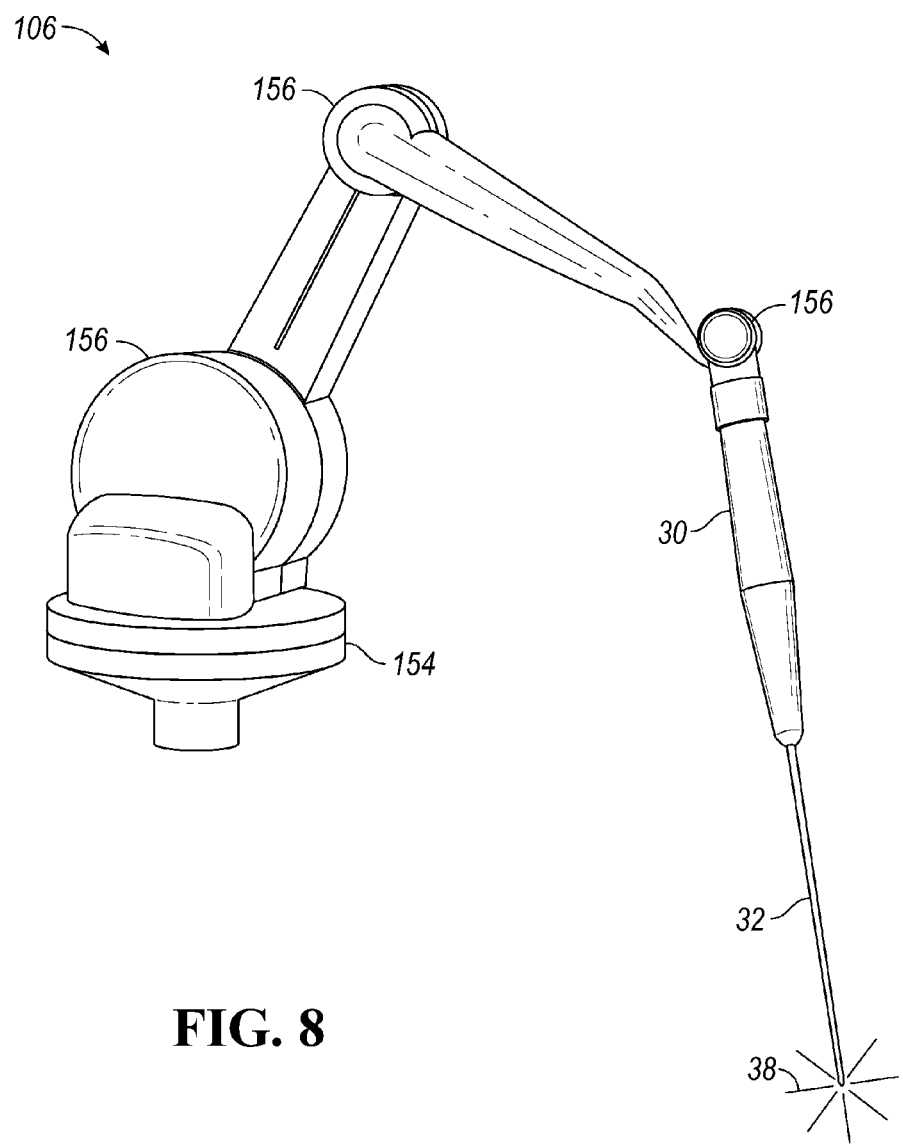
FIG. 8 is a schematic side view of a locating device that may register a stimulator in three-dimensional space.

In one embodiment, a locating device 106 used to detect the location of the one or more electrodes 34 within the physical workspace 152 may include a multi-axial, spatial input device 154 that may be affixed to the stimulator 30, and may monitor the position of the stimulator throughout the modeling procedure. An embodiment of a spatial input device 154 is generally shown in FIG. 8. In this design, the spatial input device 154 may include a plurality of instrumented rotatable joints 156, which may monitor the physical location of the stimulator 30 in three spatial dimensions (x, y, and z), as well as in three orientations (roll, pitch, and yaw). In this manner, the position of the distal end portion may be reconciled and provided to the processor 20. Commercially available examples of a spatial input device of this nature include the Touch Haptic Input Device or the Phantom Haptic Input Device, both made by Geomagic Solutions. In a similar manner, the location of the one or more electrodes 34 may be determined through the joint motion/kinematics of a surgical robot that actively controls the position and posture of the stimulator 30 throughout the procedure.

In still other embodiments, the one or more electrodes 34 may be located within the physical 3D workspace 152 by monitoring the position of the distal end portion of the stimulator 30 using a non-contact position locating device. Examples of non-contact position locating devices may use ultrasound, electrical fields, magnetic fields, fluoroscopy, or optical recognition to locate the stimulator (i.e., the distal end portion of the stimulator) within three-dimensional space.

Referring again to FIG. 7, once the relative position of the one or more electrodes 34 have been registered within the virtual workspace (at 124), and assuming that the distal tip of the stimulator 30 has been advanced to an intracorporeal location, an electric current 38 may be applied via the electrode 34 to the surrounding intracorporeal tissue (at 126). If a threshold MMG response is detected (at 128) the processor 20 may determine a distance between the electrode 34 and the nerve (at 130) and update the nerve model (at 132). Alternatively, if a threshold MMG response is not detected (at 128) the processor 20 may skip directly to updating the nerve model (at 132). As discussed above, in one configuration, determining the distance (at 130) may include directly determining the distance from a variable stim magnitude and a variable MMG response magnitude. In another configuration, determining the distance (at 130) may include determining a minimum stim current that is required to induce the threshold response at the stim location, and using that minimum inducing current to determine the distance. In such an embodiment, determining the minimum stim current may include providing one or more additional "locating" electrical stimuli of progressively decreasing intensity until the threshold response is no longer induced.

In general, the process of updating the model (at 132) involves progressively refining the voxel model to distinguish between areas that are "safe" and areas that may potentially be a nerve. FIGS. 9A-9D schematically illustrate this process. As shown, each voxel 160 within the workspace 100 may have one of three states: no-information; no-nerve (i.e., "safe"); or nerve. In one configuration, no-information may be represented by an empty or "null" value, no-nerve may be represented by a zero, and "nerve" may be represented by an integer value that is greater than or equal to one.

Figure 9B:
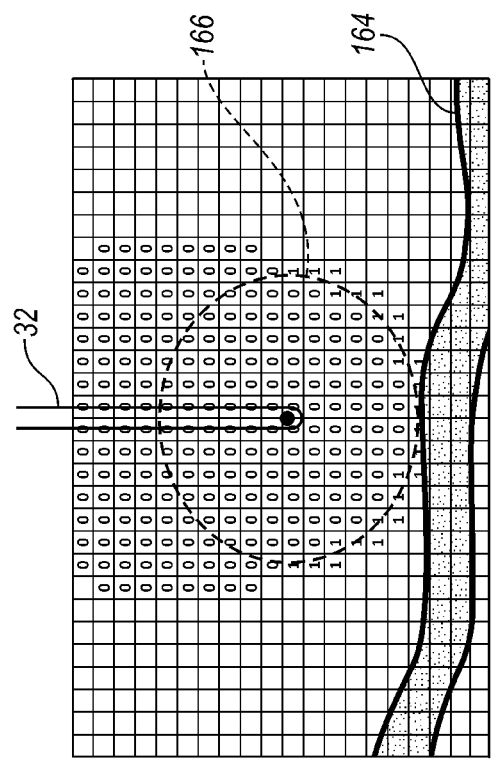
FIGS. 9A-9D are schematic 2D side views, transverse to a longitudinal axis of a stimulator, illustrating the creation of a nerve probability model using a model-based triangulation approach.
Figure 9D:
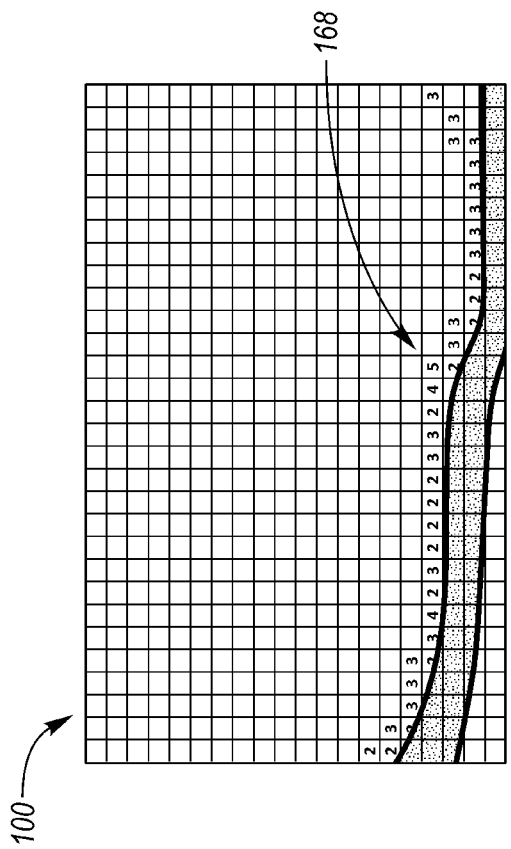
Figure 9A:
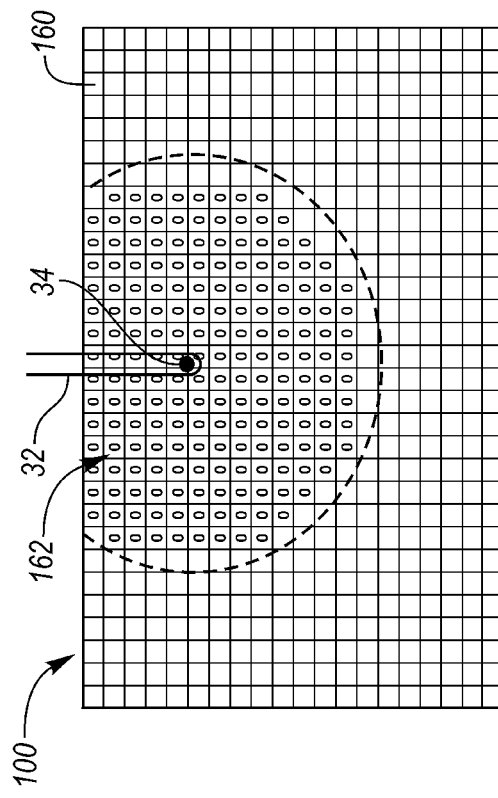

Initially, all voxels 160 may be initialized to "no-information." If a stimulus is delivered (at 126), and no threshold muscle response is measured/detected (at 128), the processor 20 may conclude that no nerve lies within a predefined radius of the electrode. As such, it may change all voxels within this area 162 to "no-nerve," such as shown in FIG. 9A and represented at 134 in FIG. 7. Once a voxel 160 is painted as "safe" (i.e., no-nerve) it should remain in that state indefinitely. If a stimulus is delivered and a nerve 164 is detected at a certain distance, such as shown in FIG. 9B, then a shell 166 may be constructed at a radius equal to the determined distance, and all voxels 160 coincident with the shell 166 would be changed to a "one" (represented at 136 in FIG. 7) (i.e., with the exception of voxels already identified as safe). Additionally, because the determined distance generally represents the minimum distance to the nerve 164, all voxels 160 interior to the shell may be deemed "safe" and changed to "no-nerve" (represented at 138 in FIG. 7).

Figure 9C:
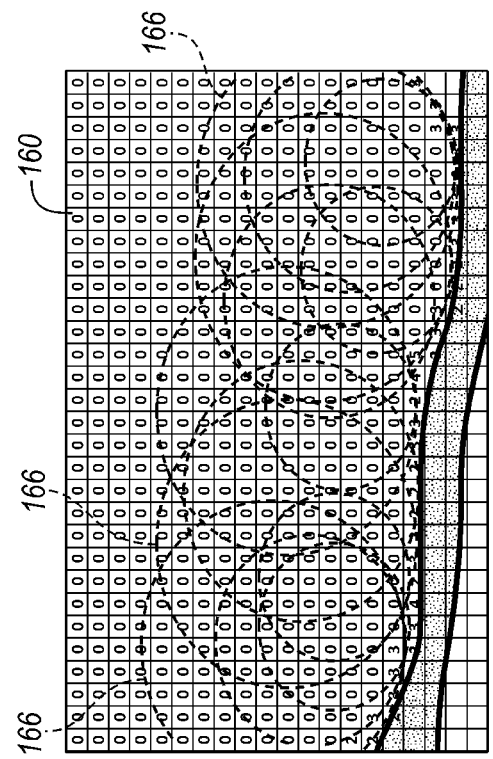

With reference to FIG. 7, after each test, if further model-refining detail is required (at 140) the electrodes 34 may be repositioned within the physical 3D workspace/intracorporeal area (at 142), and another location may be tested via the MMG stimulation routine. By sampling at many different locations, such as shown in FIG. 9C, subsequent shells 166 may be constructed, and voxels with more than one shell may be incremented to a value that reflects the number of shells at that point. Once a sufficient number of points have been tested, the voxel model may be smoothed and filtered (at 144) such that only voxels with a value above a certain threshold remain (generally represented in FIG. 9D). This remaining structure 168 provides a 3D probabilistic nerve model 100 that is representative of the actual nerve anatomy.

In one configuration, these same techniques can be used to map a plurality of different nerves concurrently. This concept of multiple nerve models would rely on a plurality of mechanical sensors distributed about the body in communication with various muscle groups, such as generally shown in FIG. 3. Each sensor may be considered its own channel that can be used to determine distances to the nerve that primarily innervates that respective group. As nerves are identified and located by the processor 20, they may be each stored in a different respective "layer" of the model 100. Upon completion of the mapping, the various distinct layers may be merged together to form the final nerve map 100.

Figure 10A:
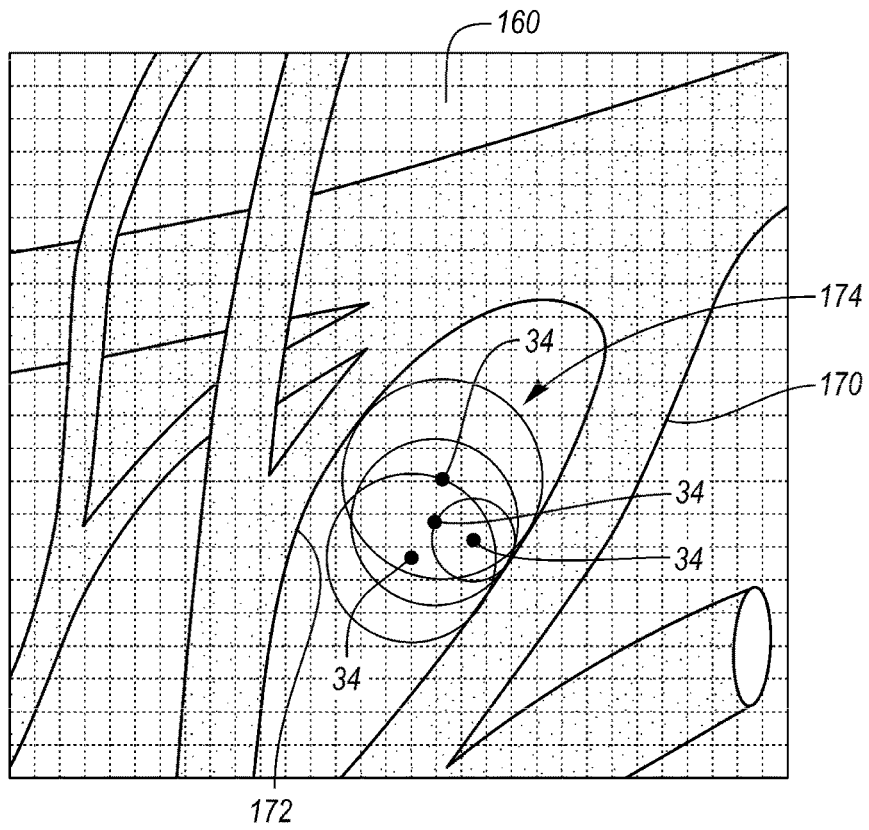
FIGS. 10A-10B are schematic 2D views along a longitudinal axis of a stimulator, illustrating model-based triangulation of multiple nerves.
Figure 10B:
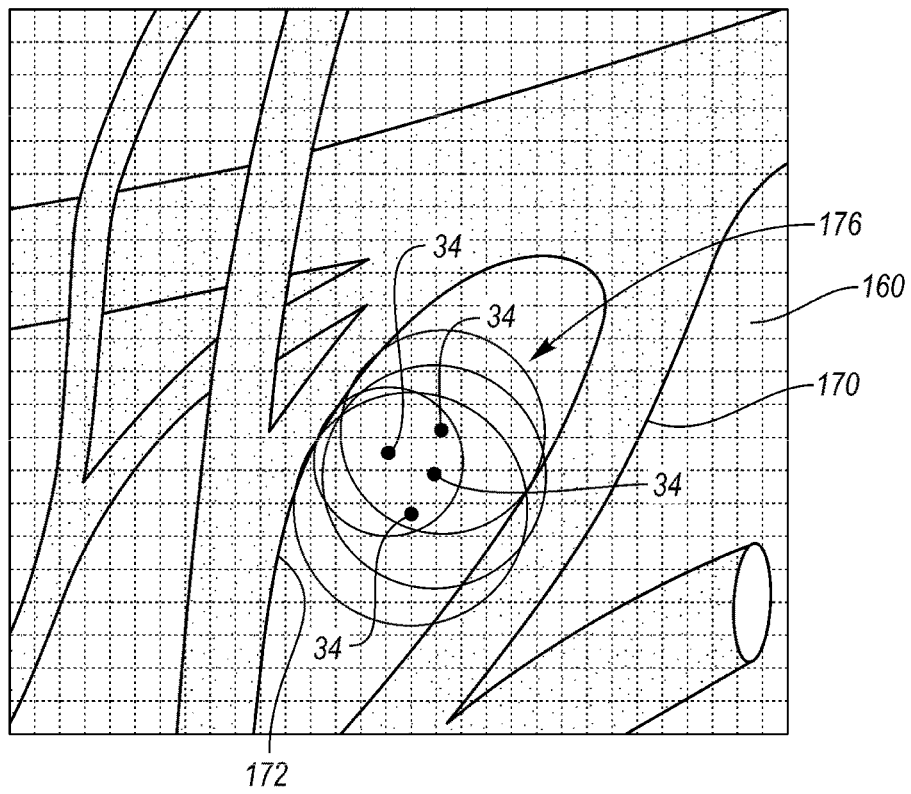

FIGS. 10A-10B schematically illustrate the multi-nerve technique being used to identify two different nerve bundles 170, 172. As shown, the system may construct a first plurality of shells 174 by identifying the mechanical response of a muscle to the simulation of the first nerve bundle 170 (shown in FIG. 10A). Either sequentially or concurrently with the creation of the first plurality of shells 174, the system may construct a second plurality of shells 176 by identifying the mechanical response of a muscle to the simulation of the second nerve bundle 176. In one configuration, each of these nerves may be separately maintained within the model to avoid having the readings of the first nerve bundle 170 erroneously affect the readings of the second nerve bundle 172 (or vice versa).

Referring again to FIG. 6, once the three dimensional nerve model 100 is created, it may be output to a display device at 112 either as a stand alone model, or by merging it with other imagery/anatomical models. For example, in one configuration, the nerve model 100 may be aligned and merged with three-dimensional CT or MRI models using anatomical landmarks/reference points, known coordinate transforms, or other such methods of merging different anatomical imaging modalities. In another configuration, a 2D view of the model may be overlaid on, for example, a 2D fluoroscope or ultrasound image. To provide enhanced clarity/visibility, the graphical overlay of the nerve model 100 may be provided in color, which would contrast against the traditionally black and white 2D image.

In another embodiment, the nerve model 100 may be output to a robotic controller 114 for the purpose of real-time guidance. More specifically, the nerve model 100 may inform the robotic controller 114 about the intracorporeal surroundings and/or may define one or more boundaries or restricted areas that constrain the motion of the end effector. In this sense, the model 100 may aid in any feedforward control (whereas any real-time MMG sensing may serve as feedback control).

In still another embodiment, the nerve model 100 may be used, together with an anatomical model, to calculate an optimal surgical approach toward an anatomical target. More specifically, the nerve model 100 may be merged with an anatomical model that is representative of the intracorporeal treatment area and a portion of the anatomical model may be identified as the "anatomical target." This target may be the ultimate destination for a surgical instrument and/or procedure, and may either generally identify a structure, such as a vertebral disk, or may more narrowly identify the specific site of the procedure.

Once an anatomical target is identified, the processor 20 may use one or more optimization routines to determine an optimal approach from an outer surface of the anatomical model to the anatomical target that minimizes the potential for contact with a nerve represented within the nerve model 100. Additionally, the optimization may account for, and minimize contact with at least one constraining/obstructing anatomical structure that lies between the outer surface of the model and the anatomical target. Examples of obstructing structures may include organs, such as the intestines, kidneys, liver, or bones, such as the ribs or pelvis/iliac crest. In a specific sense, the "optimal" approach may be the shortest linear (or non-linear) approach that reaches the anatomical target while minimizing the potential for contact with nerves or other constraining physical anatomy. Such path planning capabilities may be particularly useful when attempting to pass through areas with uncertain and/or complexly defined nerve paths, such as within the psoas muscle, when attempting to access very specific locations adjacent to critical nerves, such as docking in Kambin's triangle (a small access window to the vertebral disk that is, in part, defined by the nerve root), or when approaching locations that may be traditionally difficult to access due to obstructing anatomy, such as the L5-S1 vertebral joint.

Once an optimal path is defined, it may be displayed either alone, or overlayed/merged with an anatomical model to guide a surgeon in performing an access procedure. For example, an image of the probe (e.g., from fluoro or computer imagery) may be represented in a first manner if the probe is on the optimal path (e.g., colored green), and may be represented in a second manner if the probe is off of the optimal path (e.g., colored red). The optimal path may also (or alternatively) be passed to a robotic controller, which may constrain the motion of a robotically controlled tool and/or end effector within a predefined tolerance of the path, or may provide a fully automated approach along the path. In one configuration, the robotic controller 114 may be operative to simply constrain the motion of a tool that is under the primary (manual) control of the surgeon.

In general, the goal of the present modeling routine is to facilitate faster and safer surgical access than is possible with traditional procedures. To further this goal, in one configuration, the system may utilize an adaptive stimulation technique that can alternate between a lower resolution "searching current" and a higher resolution "locating current" to classify the intracorporeal tissue as rapidly as possible. In general, the searching current may be a higher current stimulus can more quickly characterize a large area, whereas the locating current may be a lower current stimulus that can more accurately hone in on a specific location of a nerve. These adaptive stimulation techniques are much like painting a wall with a variety of different sized brushes. While it is certainly possible to paint the entire wall with the smallest, finest brush to ensure control, it would be more efficient to paint the center of large areas with a larger brush (or roller), and switch to finer brushes only where more control and precision is required.

Figure 11:
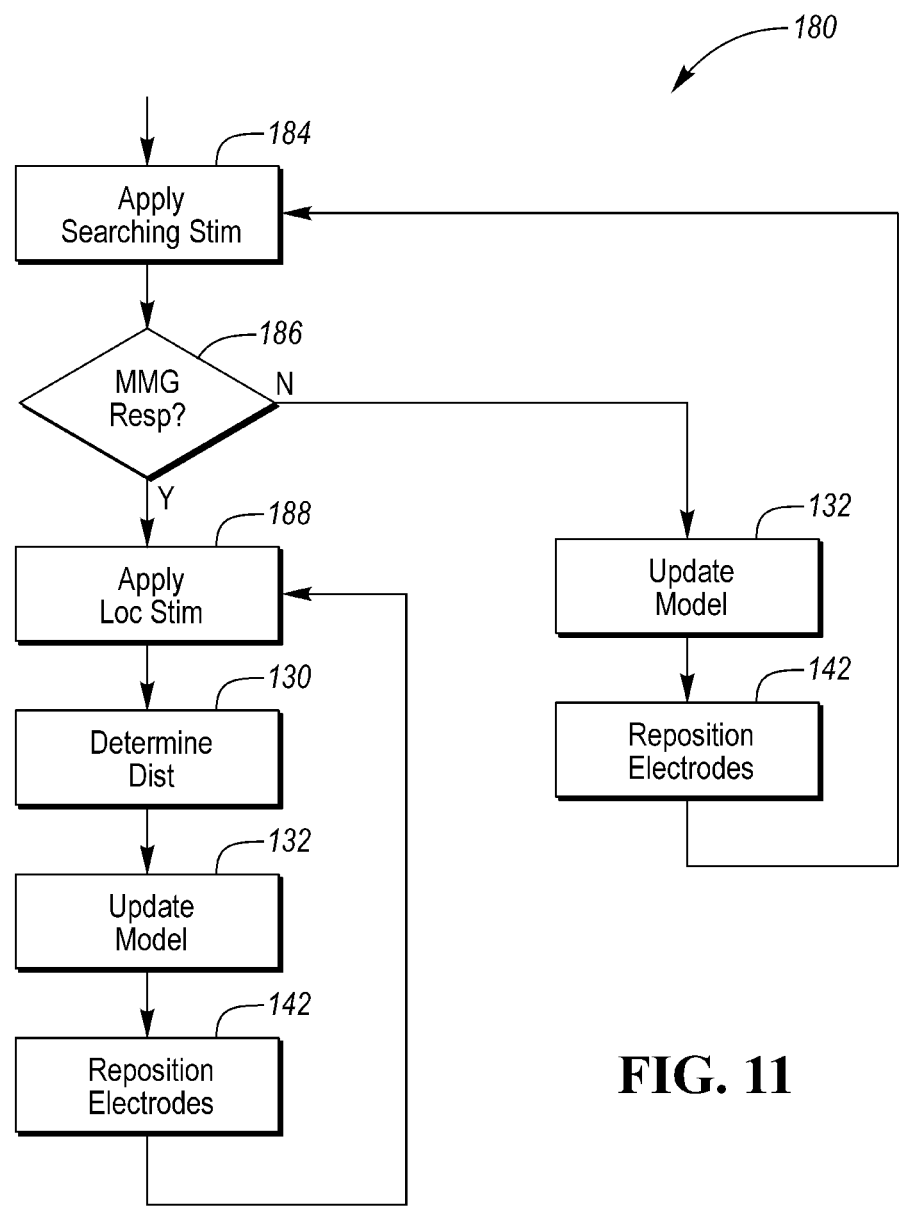
FIG. 11 is a schematic flow chart illustrating a first embodiment of an evidenced-based adaptive stimulation method.
Figure 12:
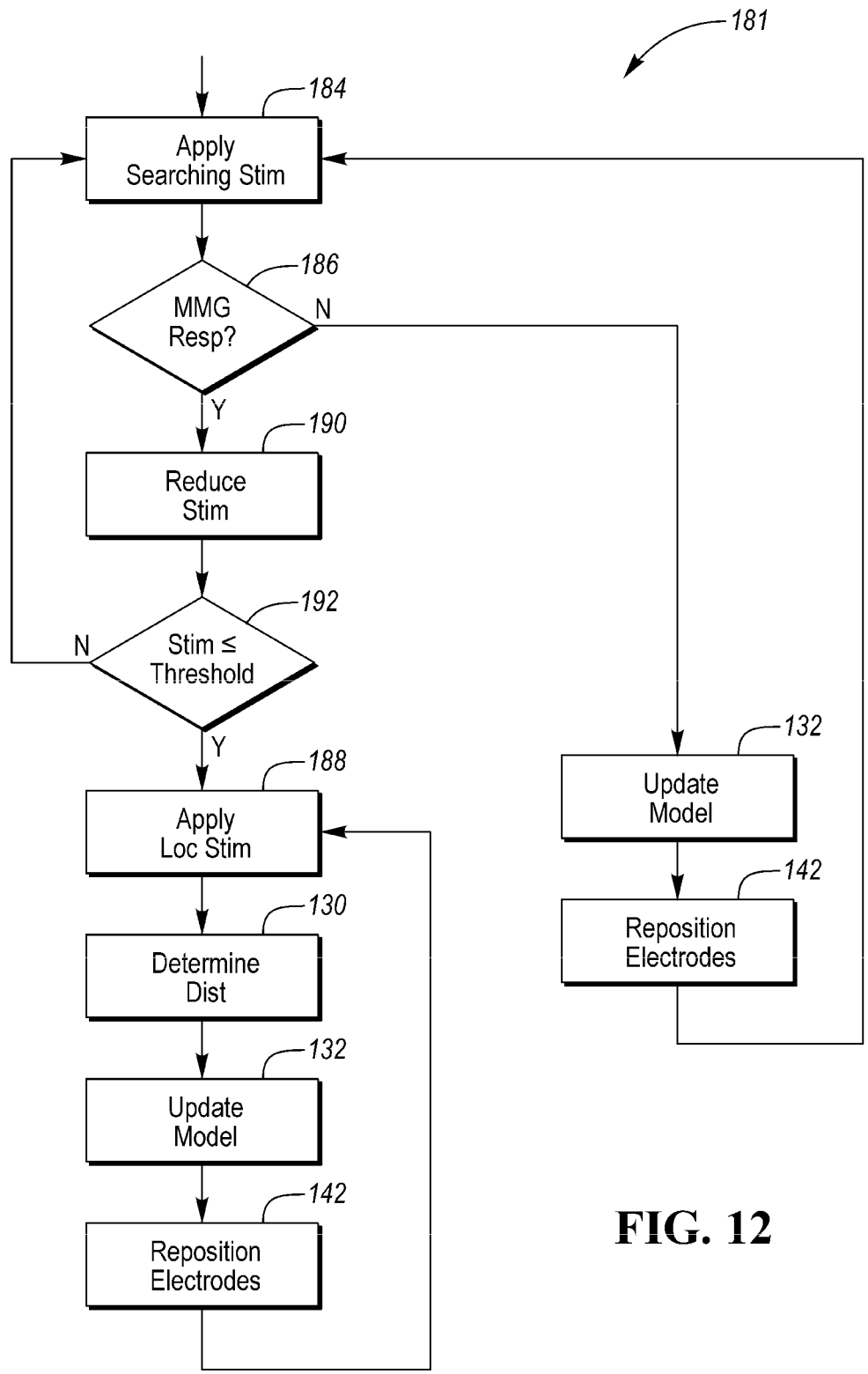
FIG. 12 is a schematic flow chart illustrating a second embodiment of an evidenced-based adaptive stimulation method.
Figure 13:
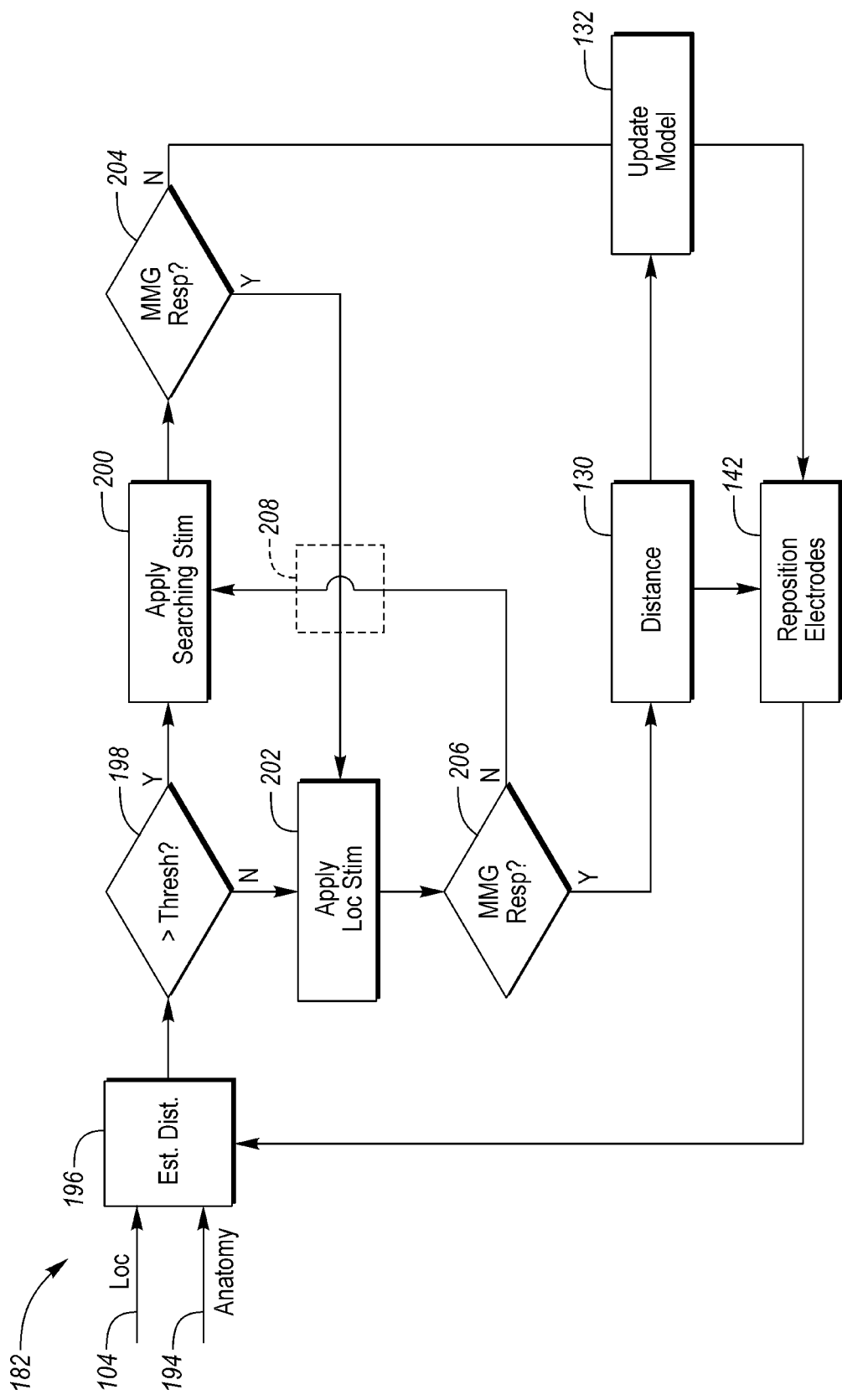
FIG. 13 is a schematic flow chart illustrating a model-based adaptive stimulation method.

FIGS. 11-13 schematically illustrate three embodiments of adaptive stimulation techniques that attempt to balance the detection speed provided by larger stim currents with the precision afforded by smaller stim currents. Specifically, FIG. 11 illustrates a first embodiment of an evidence-based adaptive stimulation method 180, FIG. 12 illustrates a second embodiment of an evidence-based adaptive stimulation method 181, and FIG. 13 illustrates a model-based adaptive stimulation method 182.

Referring to FIG. 11, the first embodiment of the evidence-based adaptive stimulation method 180 generally operates by stimulating with a larger, searching current during the approach until an MMG response is detected. In this manner, the processor 20 may paint the largest area possible as "safe" with the fewest number of stimulations/samples. Once a response is detected, the processor 20 may downshift to a smaller, locating current to more precisely locate the nerve (i.e., at the expense of speed).

As shown in FIG. 11, the method 180 begins at 184 by administering a searching stim current upon entry into the intracorporeal treatment area 12. If no MMG response is detected (at 186), then the processor 20 may update the model (at 132) as discussed above with respect to FIG. 7. The electrodes may be repositioned (at 142), and the processor 20 may re-administer the searching stimulus (at 184). If, at some point, an MMG response is detected in response to an applied searching stimulus, the processor 20 may then administer the lesser locating stim current (at 188) in an effort to more accurately determine a distance to the nerve (at 130). Once a distance is determined in response to the locating stimulus, the processor may update the model (at 132), reposition the electrodes (at 142), and then re-stim using only the lesser locating current (at 188).

In the embodiment illustrated in FIG. 12, the purpose of the "searching stimulus" is to identify safe areas, whereas the purpose of the "locating stimulus" is to identify the location of a nerve. In general, this technique contemplates that the precise location of the nerve is only relevant if it is close to the stimulator, otherwise, it is more important to know where the nerve is not located. The method 181 is similar to the method 180 shown in FIG. 11, with the exception that if an MMG response is detected (at 186) following the application of a searching stimulus, the stimulus level is reduced (at 190) and then compared to a threshold (at 192). If the reduced searching current level is still greater than the threshold (i.e., it is still sufficiently large), the reduced searching current may be reapplied (at 184) to see if the nerve response remains. If the reduced searching current level falls below the threshold (at 192) then the method 181 may downshift into a locating mode and apply the higher resolution locating stimulus in an effort to locate the nerve. In general the threshold (at 192) is a current level that defines the difference between the two modes and between a "searching stimulus" and a "locating stimulus." In one configuration, the threshold may be set by a user based on a perceived comfort with the procedure. In another configuration, the threshold may be within a range of from about 6 mA to about 12 mA. It should also be appreciated that the order of reducing the stimulus (at 190) and comparing to the threshold (at 192) is not significantly material, and can be reversed.

The model-based adaptive stimulation method 182 shown in FIG. 13 is much like the method 181 of FIG. 12, except that the processor 20 uses an indication of the location of the electrode 34, together with a general understanding of human anatomy to select whether to apply a searching stimulus or a locating stimulus given the likelihood of a proximate nerve. For example, in an area where nerves are not expected, the processor 20 may try to identify safe areas using the larger searching current. Conversely, as the stimulator/electrode approaches an area where nerves are expected (based on the anatomical model), the processor 20 may reduce the current to begin painting the area with finer resolution and/or with a better ability to accurately locate the nerve.

As shown in FIG. 13, the method 182 begins by comparing electrode location 104 with a model of neurological structure 194 (at 196) to estimate a distance between the electrode 34 and a nerve. In this embodiment, the model of neurological structure 194 may be either a previously acquired model of the actual patient (e.g., from CT or MRI), or may be a more generalized model of an "average" person.

Once the nerve distance is estimated (at 196), the estimate is then compared to a threshold (at 198) to determine whether to apply a searching current (at 200) or a locating current (at 202). The threshold may be, for example, a similar threshold as used at 192 in FIG. 12 (and/or a distance threshold that corresponds to the stimulus threshold of FIG. 12).

If the distance estimate is greater than the threshold (at 198) and the searching current is applied (at 200), the processor 20 then examines whether an MMG response was induced by the stimulus (at 204). If no MMG response is detected, then the method 182 proceeds to update the model (at 132), as no nerve is within the searching radius. If, however, a response is detected, then the processor 20 may applying a locating stimulus (at 198) to determine a distance to the unexpectedly present nerve.

If the distance estimate is less than the threshold (at 198) and the locating current is applied (at 202), the processor 20 then examines whether an MMG response was induced by the locating stimulus (at 206). If no response is detected, the processor 20 may elect to apply a searching stimulus (at 200) to further explore the area. If a response is detected to the locating stimulus, however, the processor 20 may determine a distance to the nerve (at 130) and update the model (at 132). Following the update of the model, the electrodes may be repositioned (at 142), and the process may repeat. If the processor 20 fails to sense an expected MMG response at 204 or 206, then the processor 20 may attempt to adjust the anatomical model 194 to account for the newly acquired nerve response information (at 208). For example, the processor 20 may attempt to stretch, skew, scale, or rotate portions of the anatomical model to better match the nerve model 100.

It should be appreciated that any of the adaptive stimulation techniques described with respect to FIGS. 11-13 (or variations thereof) may be used in the nerve modeling techniques described above. In particular, the nerve model 100 may operatively model the presence of one or more nerves and/or may model the absence of any nerves.

As generally illustrated in FIGS. 9C, 10A, and 10B, to properly construct a nerve model, the electrode(s) must be capable of stimulating at multiple locations throughout the intracorporeal treatment area 12. Simulation only along a single insertion axis may not provide an ability to accurately triangulate nerve position. Therefore, as illustrated in FIGS. 14A and 14B, in a first embodiment, stimulation throughout the intracorporeal treatment area 12 may be performed utilizing a plurality of thin stimulator probes 210 (e.g. K-wire style probes), each having an electrode disposed on its distal tip.

Figure 14A:
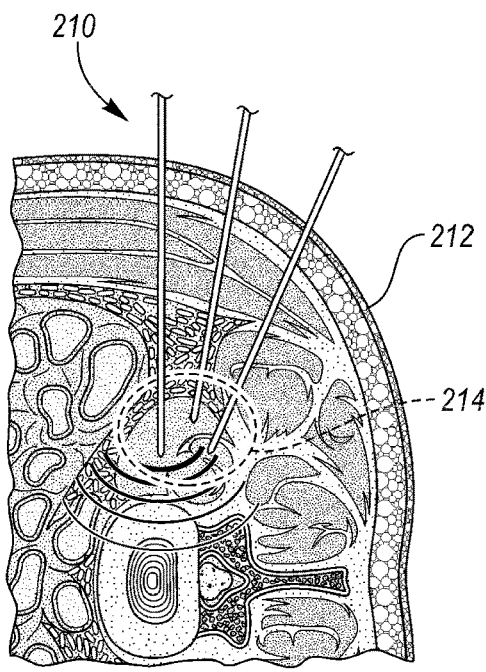
FIGS. 14A-14B are schematic transverse views of a plurality of stimulator probes being advanced toward an intracorporeal target area.

As shown in FIG. 14A, in a first configuration, each probe may be inserted through the skin 212 of the patient at a different respective location. Despite the varying entry, the probes 210 may each extend along a respective trajectory that converges toward a target location/area 214. As a slight variation on this concept, FIG. 14B illustrates the plurality of thin stimulator probes 210 extending in a closely spaced, probe array 216, where each probe 210 is parallel to the other probes. This probe array 216 may be collectively inserted through a singular incision in the skin to minimize total access points.

Figure 14B:
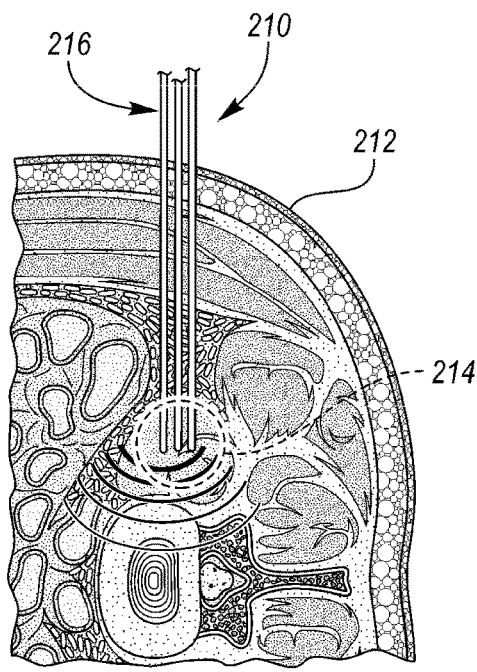

In either configuration illustrated in FIG. 14A or FIG. 14B, each probe 210 may be capable of independent movement and independent stimulation. In this manner, if one probe's trajectory is found to potentially intersect a nerve, its longitudinal progress may be halted while the remaining probes may be advanced.

Figure 15A:
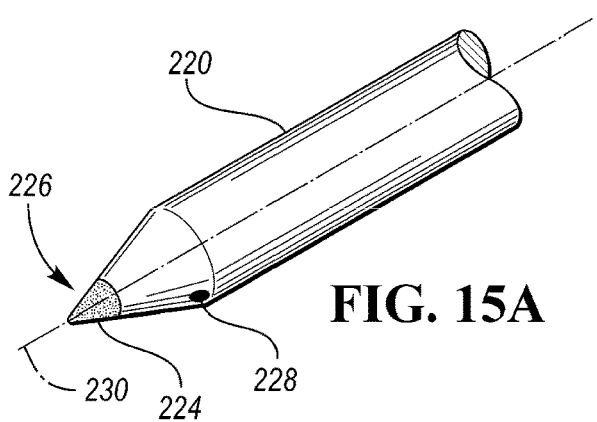
FIG. 15A is a schematic perspective view of a stimulator having a leading electrode and a single offset electrode.
Figure 15B:
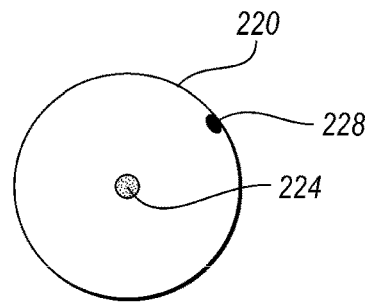
FIG. 15B is a schematic end view of the stimulator of FIG. 15A.
Figure 16A:
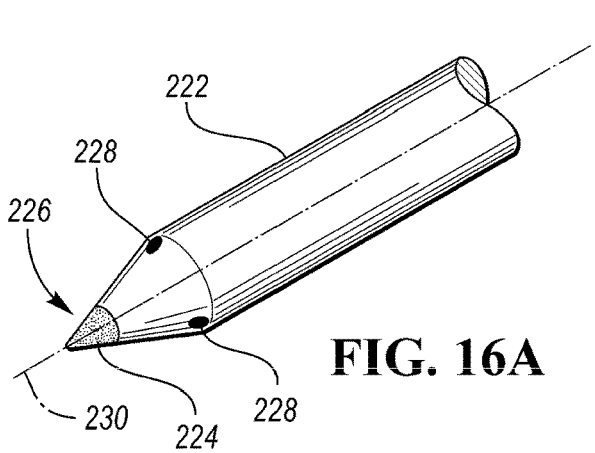
FIG. 16A is a schematic perspective view of a stimulator having a leading electrode and a plurality of offset electrodes.
Figure 16B:
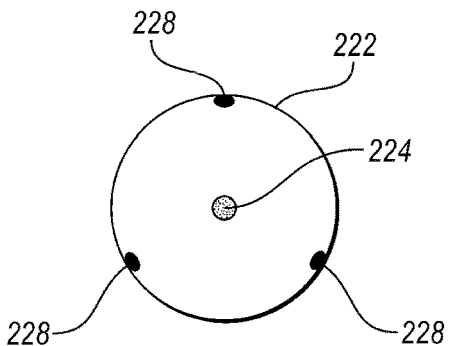
FIG. 16B is a schematic end view of the stimulator of FIG. 16A.

In another embodiment, one or more multi-electrode stimulators may be used to perform the mapping. FIGS. 15A-15B and 16A-16B illustrate two embodiments of a multi-electrode stimulator 220, 222 that may be used in the present mapping process. Each embodiment 220, 222 generally illustrates a leading electrode 224 disposed on the distal tip 226, together with one or more electrodes 228 that are offset from the stimulator's longitudinal axis 230. More specifically, the stimulator 220 shown in FIGS. 15A-15B is illustrated with a single offset electrode 228, while the stimulator 222 shown in FIGS. 16A-16B is illustrated with multiple offset electrodes 228.

In either embodiment, each electrode 224, 228 may be selectively and independently energized at the direction of a processor 20 and may be configured to provide an electrical stimulus 38 to tissue of the subject 14. Likewise, it is preferable for the electrodes 224, 228 to be disposed on the stimulator in a manner such that they make leading contact with intracorporeal tissue as the probe is being advanced in a longitudinal direction. This maximizes the likelihood that each electrode will remain in contact with the tissue.

During a mapping procedure, in one configuration, the stimulator 220 illustrated in FIGS. 15A-15B may create a 3D stimulation array by rotating the stimulator as it is longitudinally advanced. In this manner, the leading electrode 224 and offset electrode 228 may traverse a helical pattern. In another embodiment, which may provide a faster mapping procedure in some circumstances, the leading electrode 224 may be regarded as a nerve "searching electrode," while the offset electrode 228 may be a "triangulation electrode." In this embodiment, the leading/searching electrode 224 may be the sole electrode used while advancing the stimulator (i.e., the sole electrode providing the searching current). Once a nerve is detected, however, the stimulator 220 may be rotated with the offset/triangulation electrode 228 providing a locating stimulus at multiple points throughout the rotation. Such a use of the offset/triangulation electrode is generally illustrated in FIGS. 10A-10B (i.e., where multiple stimulation sites traverse an arc around a central electrode).

In another embodiment, the need to rotate the stimulator may be reduced or eliminated by including multiple offset electrodes 228, such as shown in FIGS. 16A-16B.

One embodiment of a method for utilizing the stimulators of FIGS. 15A-15B and 16A-16B involves advancing the distal end portion 36 of a stimulator 32 toward an anatomical target within the intracorporeal space. A first (searching) electrical stimulus may be applied from a leading electrode 224 disposed on a central axis 230 of the stimulator 32 while the stimulator 32 is advancing toward the anatomical target. If the processor 20 detects a response of a muscle innervated by a nerve within the intracorporeal space to the searching electrical stimulus, it may then apply a locating electrical stimulus from a plurality of locations offset from the central axis 230 of the stimulator 32. The processor 20 may then monitor a magnitude of the response of the muscle to the locating electrical stimulus at each of the plurality of locations, determine a distance between the nerve and each of the plurality of locations from the magnitude of the response and a magnitude of the locating electrical stimulus provided at each of the plurality of locations, and triangulate the location of the nerve from the determined distance at each of the plurality of locations. If the stimulator 220 of FIGS. 15A-15B is used in this method, the processor 20 may stimulate at the plurality of offset locations using the single offset electrode 228 by stimulating between successive rotations of the stimulator 220.

Figure 17:
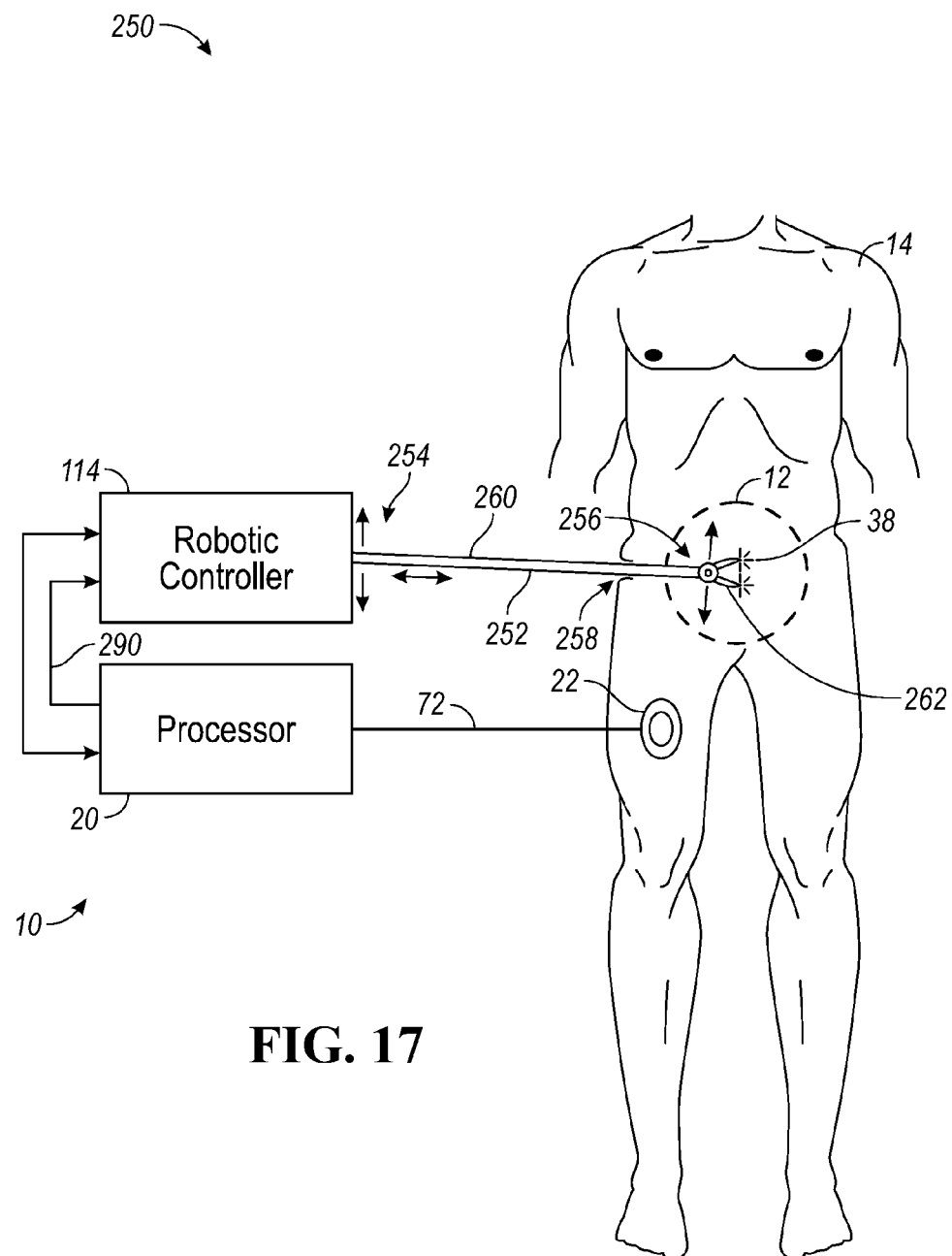
FIG. 17 is a schematic diagram of a robotically controlled surgical system for including a neural monitoring system for detecting the position of a surgical tool relative to a nerve.

FIG. 17 schematically illustrates an embodiment of a robotic surgical system 250 that may use the present nerve detection/modeling techniques. Such a system is further described in U.S. patent application Ser. No. 13/428,693, filed 23 Mar. 2012, entitled "ROBOTIC SURGICAL SYSTEM WITH MECHANOMYOGRAPHY FEEDBACK," which is incorporated by reference in its entirety and for all of the disclosure setforth therein.

As illustrated, the displayed embodiment of the robotic surgical system 250 includes a nerve detection processor 20 and a robotic controller 114. The robotic controller 114 is configured to control the motion of an elongate surgical instrument 252 that includes a proximal end portion 254 and a distal end portion 256.

During a surgical procedure, the surgical instrument 252 may extend through an opening 258 in the body of the subject 14, with the distal end portion 256 disposed within the intracorporeal treatment area 12, and the proximal end portion 254 disposed outside of the subject 14. In one configuration, the surgical instrument 252 may generally be defined by a rigid elongate body 260, such that movement of the proximal end portion 254 of the instrument 252 may result in a predictable movement of the distal end portion 256. In another configuration, the surgical instrument 252 may be defined by a controllably flexible body, such as an endoscope.

The surgical instrument 252 may further include an end effector 262 disposed at the distal end portion 256. The end effector 262 may be responsible for performing one or more cutting, grasping, cauterizing, or ablating functions, and may be selectively actuatable in at least one degree of freedom (i.e. a movable degree of freedom, such as rotation, or an electrical degree of freedom, such as selectively delivering ablative energy). Additionally, the end effector 262 may be configured to selectively rotate and/or articulate about the distal end portion 256 of the surgical instrument 252 to enable a greater range of motion/dexterity during a procedure. The end effector 262 and/or distal end portion 256 of the instrument 252 may include a plurality of electrodes (as generally discussed above, that may each be configured to provide a respective electrical stimulus 38 to tissue within the treatment area 12.

In one embodiment, such as generally illustrated in FIG. 17, the end effector 262 may be configured to resemble forceps, and may have one or more controllably movable jaws adapted to articulate about a hinged joint. The selective articulation of the one or more jaws may be enabled, for example, by cables or pull wires extending to the robotic controller through the rigid elongate body 260 of the instrument 252.

Figure 18:
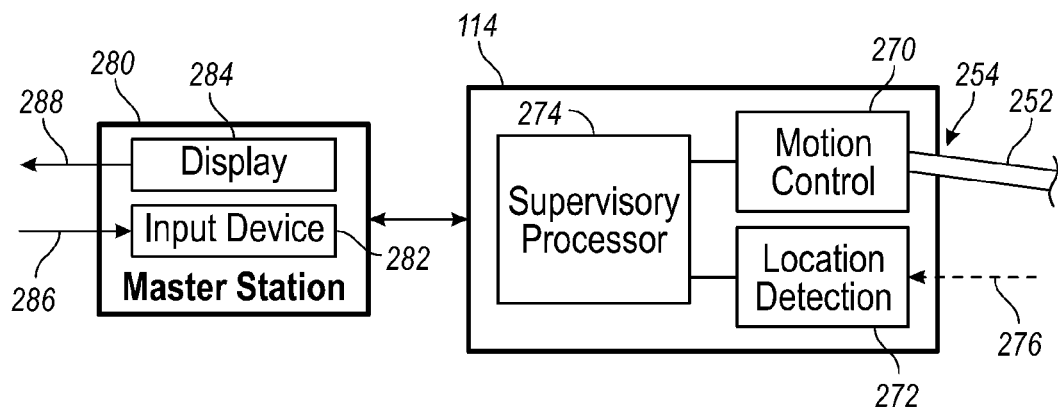
FIG. 18 is a schematic diagram of a robotic controller.

The robotic controller 114 may be responsible for controllably performing a minimally invasive surgical procedure within the body of the subject 14 by controllably manipulating the proximal end 254 of the surgical instrument 252 in a manner that results in a controlled motion of the distal end portion 256. As generally illustrated in FIG. 18, in one configuration, the robotic controller 114 may include a motion controller 270, a location detection module 272 and a supervisory processor 274. The motion controller 270 may include a plurality of motors, linear actuators, or other such components that may be required to manipulate the proximal end 254 of the surgical instrument 252 in six or more degrees of freedom. (e.g., three degrees of translation, three degrees of rotation, and/or one or more degrees of actuation). Additionally, the motion controller 270 may include one or more processors or digital computers and/or power electronics that may be required to convert a received motion command into a physical actuation of a motor or actuator.

The location detection module 272 may include one or more digital computers or processing devices that may be configured to determine the position/motion of the distal end portion 256 of the surgical instrument 252, such as relative to one or more external reference frames. In one configuration, the location detection module 272 may monitor the behavior of the motion controller 270 to determine the motion of the distal end portion 256 using kinematic relationships of the surgical instrument 252. In another configuration, the location detection module 272 may receive a location signal 276 from an external, locating device 106, which may resolve the position of the distal end portion 256 of the surgical instrument 252 using, for example, encoded joints/linkages, ultrasound energy, magnetic energy, or electromagnetic energy that may be propagated through the subject 14.

The supervisory processor 274 may be embodied as one or more digital computers or data processing devices, each having one or more microprocessors or central processing units (CPU), read only memory (ROM), random access memory (RAM), electrically-erasable programmable read only memory (EEPROM), a high-speed clock, analog-to-digital (A/D) circuitry, digital-to-analog (D/A) circuitry, input/output (I/O) circuitry, power electronics/transformers, and/or signal conditioning and buffering electronics. The individual control routines/systems resident in the supervisory processor 274 or readily accessible thereby may be stored in ROM or other suitable tangible memory location and/or memory device, and automatically executed by associated hardware components of the processor 274 to provide the respective control functionality. In one embodiment, the supervisory processor 274 may provide the motion controller 270 with actuation commands in a closed loop manner using the positional feedback provided by the location detection module 272. The supervisory processor 274 may perform any combination of feedforward, feedback, and/or predictive control schemes to accurately control the motion and/or actuation of the distal end portion 256 of the surgical instrument 252.

Additionally, the robotic controller 114 may be in communication with a master station 280 that includes a user input device 282 and a user feedback device such as a display 284 (e.g., which may be similar to display 112 provided in FIG. 6). The user input device 282 may receive an input 286 from a user that corresponds to an intended movement of the distal end portion 256 of the surgical instrument 252. The master station 280 may then provide a motion command to the robotic controller 114 that corresponds to the received input 286. Similarly, the master station 280 may receive visual information 288 from the robotic controller and convey it to the user via the display 284.

While FIG. 18 provides one embodiment of a robotic controller 114, other embodiments, configurations, and or control schemes may similarly be used to manipulate the surgical instrument 252 in a manner that results in a controlled and intended motion of the distal end portion 256. While the robotic controller 114 and surgical instrument 12 described above are generally of the kind used for robotic laparoscopy, such description is made for illustrative purposes and should not be limiting. Other minimally invasive surgical systems that employ a robotic controller 114 to control the motion of the distal end of an elongate surgical instrument may include, for example, robotic catheter systems and/or robotic endoscopic systems.

Referring again to FIG. 17, the robotic surgical system 250 includes (and/or may be in communication with) a neural monitoring system 10 that may digitally communicate with the robotic controller 114. As described above, the neural monitoring system 10 may include at least one mechanical sensor 22 and a nerve monitoring processor 20 in communication with the mechanical sensor 22. The neural monitoring system 10 may provide the robotic controller 114 with an awareness of nerves that may be adjacent to the distal end portion 256 of the surgical instrument 252. In this manner, the robotic system 250 may avoid manipulating tissue (either through translational motion or actuation of an end effector 262) that may jeopardize neural integrity.

If the nerve monitoring processor 20 detects the presence of a nerve proximate to the elongate instrument 252 (i.e., via the mechanical sensor 22), it may then provide a control signal 290 to the robotic controller 114. The control signal 290 may include an indication of the relative position/direction of the nerve, and may further include an indication of proximity between the distal end portion 256 of the surgical instrument 252 and the nerve.

Upon receipt of a control signal 290, the robotic controller 114 may artificially constrain the motion of the distal end portion 256 of the surgical instrument 252 to avoid inadvertent contact with a proximate nerve. For example, in one configuration, the robotic controller 114 may be configured to prevent all motion of the distal end portion 256 of the surgical instrument 252 in response to the received control signal 290. As such, if the distal end portion 256 was in motion, the received control signal 290 may cause the controller 114 to halt such motion and await a further command from the user. Additionally, the robotic controller 114 may be configured to limit or prevent actuation of an end effector 262 upon receipt of the control signal 290. Conversely, in certain therapeutic procedures, the robotic controller 114 may be configured to actuate the end effector 262 upon receipt of the control signal 290 (e.g., selectively deliver ablative energy to tissue proximate to the nerve).

Figure 19:
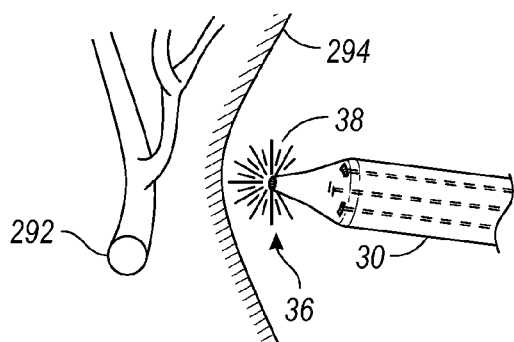
FIG. 19 is a schematic cross-sectional view of a distal end portion of an elongate surgical instrument moving with respect to a nerve of a subject.
Figure 20:
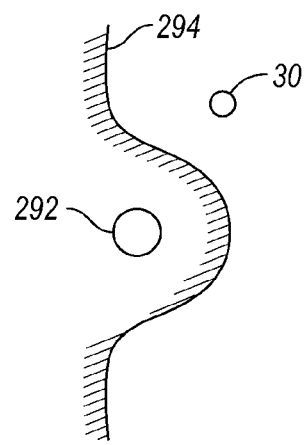
FIG. 20 is a schematic cross-sectional view of FIG. 19, with a virtual barrier being erected about the nerve.

In another configuration, such as schematically illustrated in FIG. 19, upon receipt of the control signal 290, the robotic controller may limit the instrument's ability to move in a direction toward the nerve 292. In still another configuration, the robotic controller 114 may construct a virtual barrier 294 about the nerve 292 which may prevent the instrument 252 from moving within a prescribed distance of the nerve 292. The virtual barrier 294 may be maintained in an associated memory of the robotic controller 114 and/or may be associated with the 3D nerve model 100 that may be maintained by the nerve monitoring processor 20. In general, the virtual barrier 294 may limit the allowed range of motion of the surgical instrument 252, such that the surgical instrument 252 is artificially restricted from crossing the virtual barrier 294. As generally illustrated in FIG. 20, as the surgical instrument 252 moves and acquires additional nerve directionality information, the virtual barrier 294 may be refined.

In still another configuration, once a nerve is detected, the robotic controller 114 may be configured to vary the permitted speed of the distal end portion 256 of the surgical instrument 252 as a function of the indicated proximity between the real-time location of the instrument 252 and the estimated relative position of the nerve. As such, the instrument 252 may be allowed to move more quickly and/or at a higher rate of speed when it is farther from the nerve. In this manner, the precision of the movements may be enhanced as one or more nerves become more proximate.

If the presence of a proximate nerve is detected, and/or if an action is performed by the robotic controller 114 to adjust or limit the allowed motion of the surgical instrument 252, the robotic controller 114 may likewise transmit an alert (i.e., a visual alert or an auditory alert) to the user via the master station 280.

While the above-described technology is primarily focused on determining the position of a nerve relative to a stimulator 30 and creating a nerve probability model, the nerve monitoring processor 20 may further include one or more filtering algorithms that may allow the system 10 to distinguish an artificially-induced mechanical muscle response from a patient-intended response and/or a global translation of a portion of the patient. Suitable filtering algorithms may include analog filtering algorithms, such as those described in U.S. Pat. No. 8,343,079, which is incorporated by reference in its entirety, and/or digital filtering algorithms, such as those described in U.S. Patent Application No. US2015/0051506, filed on 13 Aug. 2013 and entitled "Neural Event Detection," which is incorporated by reference in its entirety. These filtering algorithms may look at time correlations between an applied stimulus and a detected response, the rise time/slope of a monitored response, and/or frequency characteristics of the monitored response to discern whether a detected mechanical muscle movement is attributable to a provided stimulus. In one configuration, such filtering may precede any proximity detection and/or position triangulation.

While the best modes for carrying out the disclosure have been described in detail, those familiar with the art to which this disclosure relates will recognize various alternative designs and embodiments for practicing the disclosure within the scope of the appended claims. It is intended that all matter contained in the above description or shown in the accompanying drawings shall be interpreted as illustrative only and not as limiting.

The invention claimed is:

1. A nerve mapping system comprising:
   an elongate medical device including a distal end portion configured to explore an intracorporeal treatment area of a subject, the distal end portion including an electrode;
   a non-invasive mechanical sensor configured to provide a mechanomyography output signal corresponding to a monitored mechanical response of a muscle innervated by the nerve; and
   a processor in communication with the electrode and the non-invasive mechanical sensor, wherein the processor is configured to:
      provide a plurality of electrical stimuli to the electrode, each of the plurality of stimuli having a respective magnitude, and each of the plurality of stimuli provided when the electrode is located at a different respective position within the intracorporeal treatment area of the subject;
      detect a response of the muscle, via the mechanomyography output signal, to each of the plurality electrical stimuli; and
      determine the likelihood of a nerve existing at a particular point within the intercorporeal treatment area using the respective magnitudes of each of the plurality of electrical stimuli and the detected response of the muscle to each of the plurality electrical stimuli,
      wherein the plurality of electrical stimuli includes:

a first electrical stimulus provided when the electrode is at a first location within the intracorporeal treatment area, wherein the first electrical stimulus has a first current magnitude that does not induce a threshold mechanical response of the muscle;
a second electrical stimulus provided when the electrode is at a second location within the intracorporeal treatment area, wherein the second electrical stimulus has the first current magnitude; and
one or more additional electrical stimuli provided when the electrode is at the second location, wherein the one or more additional stimuli each have a current magnitude less than the first current magnitude.

2. The nerve mapping system of claim 1, further comprising a locating device operative to detect the location of the electrode within the intracorporeal treatment area;
wherein the processor is in communication with the locating device and is operative to determine the likelihood of a nerve existing at a particular point within the intercorporeal treatment area further using the detected location of the electrode when each of the respective plurality of stimuli are provided.

3. The nerve mapping system of claim 2, wherein the locating device includes at least one of a multi-axial spatial input device or a non-contact position locating device that utilizes ultrasound, electrical fields, magnetic fields, or fluoroscopy to locate the electrode within three-dimensional space.

4. The nerve mapping system of claim 1, wherein the processor is configured to maintain a virtual workspace comprising a plurality of 3-dimensional voxels, the virtual workspace being representative of the intracorporeal treatment area of the subject; and
wherein the processor is configured to determine the likelihood of a nerve existing at a particular point within the intercorporeal treatment area by:
registering the location of the electrode within the virtual workspace when each of the plurality of electrical stimuli are provided;
determining a distance between the electrode and the nerve at each respective location using the magnitude of the electrical stimuli provided at that location and the detected response of the muscle to the electrical stimuli provided at that location;
incrementing a counter associated with each voxel that is the determined distance from the registered locations;
resetting the counter associated with each voxel that is less than the determined distance from the registered locations; and
filtering out all voxels with a counter below a predetermined threshold to generate a nerve model.

5. The nerve mapping system of claim 4, wherein the processor is further configured to merge the nerve model with a CT, MRI, fluoroscope, or ultrasound image.

6. The nerve mapping system of claim 1, further comprising a locating device operative to monitor the location of the distal end portion of the elongate medical device;
wherein the processor is further configured to estimate a distance estimate between the monitored location and the nerve using a previously acquired anatomical model;
select the first current magnitude using the estimated distance;
determine, from the one or more additional electrical stimuli, a minimum current magnitude required to induce a threshold mechanical response of the muscle at the second location; and
determine a distance from the second location to the nerve using the determined minimum current magnitude.

7. The nerve mapping system of claim 6, wherein the first current magnitude is selected from a bounded current range and is the largest current within the bounded current range that is expected to not induce the mechanical response of the muscle when applied at the estimated distance from the nerve.

8. The nerve mapping system of claim 1, wherein each of the electrical stimuli provided to the electrode are transmitted to the intracorporeal treatment area in an omnidirectional manner.

9. A nerve mapping system comprising:
an elongate medical device including:
a distal end portion configured to explore an intracorporeal treatment area of a subject;
a central axis intersecting the distal end portion and extending through a center of the elongate medical device;
a first electrode disposed in a first location at the distal end portion of the elongate medical device and on the central axis; and
at least one second electrode spaced apart from the first electrode and radially offset from the central axis in a second location; and
a non-invasive mechanical sensor configured to provide a mechanomyography output signal corresponding to a monitored mechanical response of a muscle innervated by the nerve; and
a processor in communication with the electrode and the non-invasive mechanical sensor, wherein the processor is configured to:
provide a plurality of electrical stimuli to the elongate medical device, wherein at least one stimulus of the plurality of electrical stimuli is provided to the first electrode and at least one stimulus of the plurality of electrical stimuli is provided to the at least one second electrode, each of the plurality of stimuli having a respective magnitude, and each of the plurality of stimuli provided when the elongate medical device is located at a different respective position within the intracorporeal treatment area of the subject;
detect a response of the muscle, via the mechanomyography output signal, to each of the plurality electrical stimuli; and
determine the likelihood of a nerve existing at a particular point within the intercorporeal treatment area using the respective magnitudes of each of the plurality of electrical stimuli and the detected response of the muscle to each of the plurality electrical stimuli.

10. A nerve mapping system comprising:
an elongate medical device configured to explore an intracorporeal treatment area of a subject, the elongate medical device including:
a distal end portion
a central axis intersecting the distal end portion and extending through a center of the elongate medical device;
an electrode disposed at an end of the elongate medical device and on the central axis; and a non-invasive mechanical sensor configured to provide a mechanomyography output signal corresponding to a monitored mechanical response of a muscle innervated by the nerve; and a processor in communication with the first and second electrodes and with the non-invasive mechanical sensor, wherein the processor is configured to:

provide a first electrical stimulus to the first electrode when the first electrode is at a first location within the intracorporeal treatment area, wherein the first electrical stimulus has a first current magnitude that is selected such that it does not induce a threshold mechanical response of the muscle;

provide a second electrical stimulus to the first electrode when the first electrode is at a second location within the intracorporeal treatment area, wherein the second electrical stimulus has the first current magnitude;

provide one or more additional electrical stimuli to the first or the second electrode when the first electrode is at the second location, wherein the one or more additional stimuli each have a current magnitude less than the first current magnitude;

monitor the mechanomyography output signal following the providing of each electrical stimulus;

determine, from the one or more additional electrical stimuli, a minimum current magnitude required to induce the threshold mechanical response of the muscle at the second location; and determine a distance from the second location to the nerve using the determined minimum current magnitude.

11. The nerve mapping system of claim 10, wherein the processor is configured to select the first magnitude from a bounded current range such that it is the largest current within the bounded current range that is expected to not induce the mechanical response of the muscle when applied at an estimated distance between the first location and the nerve.

12. The nerve mapping system of claim 11, wherein the processor is configured to estimate the distance between the first location and the nerve by monitoring the location of the electrode within the intracorporeal treatment area, and by comparing the estimated distance to an anatomical model.

13. The nerve mapping system of claim 12, further comprising a locating device operative to detect the location of the electrode within the intracorporeal treatment area;

wherein the processor is in communication with the locating device and is operative to monitor the location of the electrode within the intracorporeal treatment area via the locating device.

14. The nerve mapping system of claim 13, wherein the locating device includes at least one of a multi-axial spatial input device or a non-contact position locating device that utilizes ultrasound, electrical fields, magnetic fields, or fluoroscopy to locate the electrode within three-dimensional space.

15. The nerve mapping system of claim 10, wherein the processor is further configured to:

register each of the first location and the second location within a virtual workspace;

indicate a portion of the virtual workspace surrounding the first location as not containing the nerve; and indicate the presence of a nerve within the virtual workspace at the determined distance from the second location.

16. The nerve mapping system of claim 15, wherein the processor is further configured to indicate a second portion of the virtual workspace as not containing the nerve, wherein the second portion surrounds the second location up to the determined distance.

17. The nerve mapping system of claim 15, wherein the processor is further configured to merge the virtual workspace with a CT, MRI, fluoroscope, or ultrasound image.

* * * * *